US012767725B2

(12) United States Patent
Lin et al.

(10) Patent No.: US 12,767,725 B2
(45) Date of Patent: Oct. 20, 2026

(54) SINGLE-CHAIN FRAGMENT VARIABLE COMPRISING MUTANT LIGHT CHAIN FRAMEWORK REGION

(71) Applicant: BEIJING MABWORKS BIOTECH CO., LTD, Beijing (CN)

(72) Inventors: Guangzhong Lin, Beijing (CN); Jiangmei Li, Beijing (CN); Wenqi Hu, Beijing (CN); Feng Li, Beijing (CN)

(73) Assignee: BEIJING MABWORKS BIOTECH CO., LTD, Beijing (CN)

( * ) Notice: Subject to any disclaimer, the term of this patent is extended or adjusted under 35 U.S.C. 154(b) by 745 days.

(21) Appl. No.: 18/307,357

(22) Filed: Apr. 26, 2023

(65) Prior Publication Data

US 2023/0348612 A1 Nov. 2, 2023

(30) Foreign Application Priority Data

Apr. 28, 2022 (CN) ......................... 202210463614.8

(51) Int. Cl.
*C07K 16/28* (2006.01)

(52) U.S. Cl.
CPC .......... *C07K 16/2887* (2013.01); *C07K 16/28* (2013.01); *C07K 16/2809* (2013.01); *C07K 2317/31* (2013.01); *C07K 2317/622* (2013.01); *C07K 2317/92* (2013.01); *C07K 2317/94* (2013.01)

(58) Field of Classification Search
CPC ................ C07K 16/28; C07K 16/2887; C07K 16/2809; C07K 16/22; C07K 16/2803; C07K 2317/31; C07K 2317/622; C07K 2317/92; C07K 2317/94; C07K 2317/35; C07K 2317/52; C07K 2317/64; C07K 2317/55; C07K 2317/56; C07K 2317/565; C07K 2317/567; A61P 35/00; A61P 35/02; A61P 37/02; A61K 2039/505
See application file for complete search history.

(56) References Cited

U.S. PATENT DOCUMENTS

| | | | | |
|---|---|---|---|---|
| 11,459,405 | B2 * | 10/2022 | Sasisekharan | C07K 16/2863 |
| 12,180,280 | B2 * | 12/2024 | Li | C07K 16/2887 |
| 2003/0059937 | A1 | 3/2003 | Ruben et al. | |
| 2007/0071745 | A1 * | 3/2007 | Umana | A61P 7/06 530/388.25 |
| 2009/0155250 | A1 | 6/2009 | Purcell et al. | |
| 2023/0355672 | A1 * | 11/2023 | Wälchli | C07K 14/7051 |

FOREIGN PATENT DOCUMENTS

| | | | | |
|---|---|---|---|---|
| CN | 102753193 A | | 10/2012 | |
| EP | 2281843 A1 | | 2/2011 | |
| EP | 2592094 A1 | | 5/2013 | |
| WO | WO-2008099188 A1 | * | 8/2008 | A61P 37/08 |
| WO | 2016020309 A1 | | 2/2016 | |
| WO | WO-2022134645 A1 | * | 6/2022 | A61P 37/02 |

OTHER PUBLICATIONS

Lehmann et al., Stability engineering of anti-EGFR scFv antibodies by rational design of a lambda-to-kappa swap of the VL framework using a structure-guided approach, 2015, mAbs, 7(6):1058-1071. (Year: 2015).*
Salvaris et al., Bispecific Antibodies: A Review of Development, Clinical Efficacy and Toxicity in B-Cell Lymphomas, 2021, J. Pers. Med, 11(355):1-15 (Year: 2021).*
Tanaka et al., Intrabodies based on intracellular capture frameworks that bind the RAS protein with high affinity and impair oncogenic transformation, 2003, The EMBO Journal, 22(5):1025-1035. (Year: 2003).*
EPO, Supplementary European Search Report and Written Opinion, issued to counterpart EP application, Feb. 26, 2026.
Bock Allison M et al., Bispecific Antibodies for Non-Hodgkin Lymphoma Treatment, Current Treatment Options in Oncology, vol. 23, No. 2, Feb. 1, 2022, p. 155-170.
Cnudde Thomas et al., Exploration and Modulation of Antibody Fragment Biophysical Properties by Replacing the Framework Region Sequences, Antibodies, vol. 9, No. 2, Apr. 15, 2020, p. 9.
Ulrich Brinkmann et al., The making of bispecific antibodies, MABS, vol. 9, No. 2, Jan. 10, 2017, p. 182-212.
Karen J. Vincent et al., Current Strategies in antibody engineering: Fc engineering and pH-dependent antigen binding, bispecific antibodies and antibody drug conjugates, BiotechnologyJournal, vol. 7, No. 12, Dec. 1, 2012, pp. 1444-1450.
International Searching Authority, International Search Report and Written Opinion, issued to counterpart international application PCT/CN2023/090747, Aug. 10, 2023.

* cited by examiner

*Primary Examiner* — Julie Wu
*Assistant Examiner* — Jieun Ham
(74) *Attorney, Agent, or Firm* — Duane Morris LLP; Thomas J. Kowalski

(57) ABSTRACT

Disclosed is a single chain fragment variable (scFv), comprising a heavy chain variable region, a linker and a κ light chain variable region, wherein the κ light chain variable region is engineered to comprise leucin (L), threonine (T) and alanine (A) at Position 104 to 106 according to the Kabat numbering scheme.

13 Claims, 3 Drawing Sheets

Specification includes a Sequence Listing.

SEQUENCE LISTING

```
Sequence total quantity: 39
SEQ ID NO: 1           moltype = AA  length = 5
FEATURE                Location/Qualifiers
source                 1..5
                       mol_type = protein
                       organism = synthetic construct
SEQUENCE: 1
TYAMN                                                        5

SEQ ID NO: 2           moltype = AA  length = 17
FEATURE                Location/Qualifiers
source                 1..17
                       mol_type = protein
                       organism = synthetic construct
SEQUENCE: 2
RIRSKYNNYA TYYAISV                                           17
```

```
SEQ ID NO: 3            moltype = AA  length = 14
FEATURE                 Location/Qualifiers
source                  1..14
                        mol_type = protein
                        organism = synthetic construct
SEQUENCE: 3
HGNFGNSYLS YWAY                                                  14

SEQ ID NO: 4            moltype = AA  length = 14
FEATURE                 Location/Qualifiers
source                  1..14
                        mol_type = protein
                        organism = synthetic construct
SEQUENCE: 4
QSSTGAVTTN NYAN                                                  14

SEQ ID NO: 5            moltype = AA  length = 7
FEATURE                 Location/Qualifiers
source                  1..7
                        mol_type = protein
                        organism = synthetic construct
SEQUENCE: 5
GTKQRAP                                                          7

SEQ ID NO: 6            moltype = AA  length = 9
FEATURE                 Location/Qualifiers
source                  1..9
                        mol_type = protein
                        organism = synthetic construct
SEQUENCE: 6
VLWYSNLWV                                                        9

SEQ ID NO: 7            moltype = AA  length = 5
FEATURE                 Location/Qualifiers
source                  1..5
                        mol_type = protein
                        organism = synthetic construct
SEQUENCE: 7
YSWIN                                                            5

SEQ ID NO: 8            moltype = AA  length = 15
FEATURE                 Location/Qualifiers
source                  1..15
                        mol_type = protein
                        organism = synthetic construct
SEQUENCE: 8
RIFPGDGDTD YNGKF                                                 15

SEQ ID NO: 9            moltype = AA  length = 10
FEATURE                 Location/Qualifiers
source                  1..10
                        mol_type = protein
                        organism = synthetic construct
SEQUENCE: 9
NVFDGYWLVY                                                       10

SEQ ID NO: 10           moltype = AA  length = 16
FEATURE                 Location/Qualifiers
source                  1..16
                        mol_type = protein
                        organism = synthetic construct
SEQUENCE: 10
RSSKSLLHSN GITYLY                                                16

SEQ ID NO: 11           moltype = AA  length = 7
FEATURE                 Location/Qualifiers
source                  1..7
                        mol_type = protein
                        organism = synthetic construct
SEQUENCE: 11
QMSNLVS                                                          7

SEQ ID NO: 12           moltype = AA  length = 9
FEATURE                 Location/Qualifiers
source                  1..9
                        mol_type = protein
                        organism = synthetic construct
SEQUENCE: 12
AQNLELPYT                                                        9
```

```
SEQ ID NO: 13          moltype = AA  length = 125
FEATURE                Location/Qualifiers
source                 1..125
                       mol_type = protein
                       organism = synthetic construct
SEQUENCE: 13
EVQLLESGGG LVQPGGSLRL SCAASGFTFN TYAMNWVRQA PGKGLEWVAR IRSKYNNYAT  60
YYAISVKDRF TISRDDSKNT LYLQMNSLRA EDTAMYYCVR HGNFGNSYLS YWAYWGQGTL  120
VTVSS                                                              125

SEQ ID NO: 14          moltype = AA  length = 109
FEATURE                Location/Qualifiers
source                 1..109
                       mol_type = protein
                       organism = synthetic construct
SEQUENCE: 14
QAVVTQEPSL TVSPGGTVTL TCQSSTGAVT TNNYANWVQQ KPGHAFRGLI GGTKQRAPGV  60
PARFSGSLLG GKAALTLSGV QPEDEAEYYC VLWYSNLWVF GGGTKLTVL              109

SEQ ID NO: 15          moltype = AA  length = 119
FEATURE                Location/Qualifiers
source                 1..119
                       mol_type = protein
                       organism = synthetic construct
SEQUENCE: 15
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 16          moltype = AA  length = 112
FEATURE                Location/Qualifiers
source                 1..112
                       mol_type = protein
                       organism = synthetic construct
VARIANT                88
                       note = V or E
VARIANT                105
                       note = G or Q
VARIANT                109
                       note = V or L
VARIANT                110
                       note = E or T
VARIANT                111
                       note = I or A
SEQUENCE: 16
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDXGV YYCAQNLELP YTFGXGTKXX XK          112

SEQ ID NO: 17          moltype = AA  length = 106
FEATURE                Location/Qualifiers
source                 1..106
                       mol_type = protein
                       organism = synthetic construct
SEQUENCE: 17
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 18          moltype = AA  length = 107
FEATURE                Location/Qualifiers
source                 1..107
                       mol_type = protein
                       organism = synthetic construct
SEQUENCE: 18
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 19          moltype = AA  length = 330
FEATURE                Location/Qualifiers
source                 1..330
                       mol_type = protein
                       organism = synthetic construct
VARIANT                249
                       note = W or S
VARIANT                251
                       note = L or A
VARIANT                290
                       note = Y or V
SEQUENCE: 19
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLXC XVKGFYPSDI AVEWESNGQP ENNYKTTPPV LDSDGSFFLX SKLTVDKSRW  300
QQGNVFSCSV MHEALHNHYT QKSLSLSPGK                                   330

SEQ ID NO: 20          moltype = AA  length = 721
FEATURE                Location/Qualifiers
source                 1..721
                       mol_type = protein
                       organism = synthetic construct
VARIANT                227
                       note = E or V
VARIANT                244
                       note = Q or G
VARIANT                248
                       note = L or V
VARIANT                249
                       note = T or E
VARIANT                250
                       note = A or I
SEQUENCE: 20
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSG  120
GGGSGGGGSG GGGSGGGGSD IVMTQTPLSL PVTPGEPASI SCRSSKSLLH SNGITYLYWY  180
LQKPGQSPQL LIYQMSNLVS GVPDRFSGSG SGTDFTLKIS RVEAEDXGVY YCAQNLELPY  240
TFGXGTKXXX KGGGGSGGGG SGGGGSEVQL LESGGGLVQP GGSLRLSCAA SGFTFNTYAM  300
NWVRQAPGKG LEWVARIRSK YNNYATYYAI SVKDRFTISR DDSKNTLYLQ MNSLRAEDTA  360
MYYCVRHGNF GNSYLSYWAY WGQGTLVTVS SASTKGPSVF PLAPSSKSTS GGTAALGCLV  420
KDYFPEPVTV SWNSGALTSG VHTFPAVLQS SGLYSLSSVV TVPSSSLGTQ TYICNVNHKP  480
SNTKVDKKVE PKSCDKTHTC PPCPAPEAAG GPSVFLFPPK PKDTLMISRT PEVTCVVVDV  540
SHEDPEVKFN WYVDGVEVHN AKTKPREEQY ASTYRVVSVL TVLHQDWLNG KEYKCKVSNK  600
ALPAPIEKTI SKAKGQPREP QVYTLPPSRE EMTKNQVSLW CLVKGFYPSD IAVEWESNGQ  660
PENNYKTTPP VLDSDGSFFL YSKLTVDKSR WQQGNVFSCS VMHEALHNHY TQKSLSLSPG  720
K                                                                  721

SEQ ID NO: 21          moltype = AA  length = 449
FEATURE                Location/Qualifiers
source                 1..449
                       mol_type = protein
                       organism = synthetic construct
SEQUENCE: 21
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYAS  300
TYRVVSVLTV LHQDWLNGKE YKCKVSNKAL PAPIEKTISK AKGQPREPQV YTLPPSREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                    449

SEQ ID NO: 22          moltype = AA  length = 215
FEATURE                Location/Qualifiers
source                 1..215
                       mol_type = protein
                       organism = synthetic construct
SEQUENCE: 22
QAVVTQEPSL TVSPGGTVTL TCQSSTGAVT TNNYANWVQQ KPGHAFRGLI GGTKQRAPGV  60
PARFSGSLLG GKAALTLSGV QPEDEAEYYC VLWYSNLWVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 23          moltype = AA  length = 219
FEATURE                Location/Qualifiers
source                 1..219
                       mol_type = protein
                       organism = synthetic construct
SEQUENCE: 23
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 24          moltype = AA  length = 110
FEATURE                Location/Qualifiers
source                 1..110
                       mol_type = protein
                       organism = synthetic construct
VARIANT                84
```

```
                         note = F or E
VARIANT                  107
                         note = E or T
VARIANT                  108
                         note = L or A
SEQUENCE: 24
EIVLTQSPGT LSLSPGERAT MTCRASSSIS STYLHWYQQK PGASPKLLIY NTQNLASGVP  60
ARFSGSGSGT SYTLTISRLE PEDXAVYYCQ QFGGYPLITF GAGTKLXXKR             110

SEQ ID NO: 25            moltype = AA  length = 713
FEATURE                  Location/Qualifiers
source                   1..713
                         mol_type = protein
                         organism = synthetic construct
VARIANT                  687
                         note = F or E
VARIANT                  710
                         note = E or T
VARIANT                  711
                         note = L or A
SEQUENCE: 25
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGAGGGGSGG GGSGGGGSQV QLVQSGAEVK  480
KPGASVKVSC KASGYTFTSY NVHWVRQAPG QGLEWMGTIY PGNLATSYNQ KFKGRVTLTA  540
DTSTSTVYME LSSLRSEDTA VYYCARSGTM DYWGQGTTVT VSSGGGGSGG GGSGGGGSGG  600
GGSEIVLTQS PGTLSLSPGE RATMTCRASS SISSTYLHWY QQKPGASPKL LIYNTQNLAS  660
GVPARFSGSG SGTSYTLTIS RLEPEDXAVY YCQQFGGYPL ITFGAGTKLX XKR         713

SEQ ID NO: 26            moltype = AA  length = 214
FEATURE                  Location/Qualifiers
source                   1..214
                         mol_type = protein
                         organism = synthetic construct
SEQUENCE: 26
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 27            moltype = AA  length = 15
FEATURE                  Location/Qualifiers
source                   1..15
                         mol_type = protein
                         organism = synthetic construct
SEQUENCE: 27
GGGGSGGGGS GGGGS                                                   15

SEQ ID NO: 28            moltype = AA  length = 20
FEATURE                  Location/Qualifiers
source                   1..20
                         mol_type = protein
                         organism = synthetic construct
SEQUENCE: 28
GGGGSGGGGS GGGGSGGGGS                                              20

SEQ ID NO: 29            moltype = AA  length = 25
FEATURE                  Location/Qualifiers
source                   1..25
                         mol_type = protein
                         organism = synthetic construct
SEQUENCE: 29
GGGGSGGGGS GGGGSGGGGS GGGGS                                        25

SEQ ID NO: 30            moltype = AA  length = 716
FEATURE                  Location/Qualifiers
source                   1..716
                         mol_type = protein
                         organism = synthetic construct
SEQUENCE: 30
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSSG  120
GGGSGGGGSG GGGSDIVMTQ TPLSLPVTPG EPASISCRSS KSLLHSNGIT YLYWYLQKPG  180
QSPQLLIYQM SNLVSGVPDR FSGSGSGTDF TLKISRVEAE DVGVYYCAQN LELPYTFGGG  240
```

```
TKVEIKGGGG SGGGGSGGGG SEVQLLESGG GLVQPGGSLR LSCAASGFTF NTYAMNWVRQ  300
APGKGLEWVA RIRSKYNNYA TYYAISVKDR FTISRDDSKN TLYLQMNSLR AEDTAMYYCV  360
RHGNFGNSYL SYWAYWGQGT LVTVSSASTK GPSVFPLAPS SKSTSGGTAA LGCLVKDYFP  420
EPVTVSWNSG ALTSGVHTFP AVLQSSGLYS LSSVVTVPSS SLGTQTYICN VNHKPSNTKV  480
DKKVEPKSCD KTHTCPPCPA PEAAGGPSVF LFPPKPKDTL MISRTPEVTC VVVDVSHEDP  540
EVKFNWYVDG VEVHNAKTKP REEQYASTYR VVSVLTVLHQ DWLNGKEYKC KVSNKALPAP  600
IEKTISKAKG QPREPQVYTL PPSREEMTKN QVSLWCLVKG FYPSDIAVEW ESNGQPENNY  660
KTTPPVLDSD GSFFLYSKLT VDKSRWQQGN VFSCSVMHEA LHNHYTQKSL SLSPGK      716

SEQ ID NO: 31          moltype = AA  length = 244
FEATURE                Location/Qualifiers
source                 1..244
                       mol_type = protein
                       organism = synthetic construct
SEQUENCE: 31
MRWCLLLIWA QGLRQAPLAS GMMTGTIETT GNISAEKGGS IILQCHLSST TAQVTQVNWE  60
QQDQLLAICN ADLGWHISPS FKDRVAPGPG LGLTLQSLTV NDTGEYFCIY HTYPDGTYTG  120
RIFLEVLESS VAEHGARFQI PLLGAMAATL VVICTAVIVV VALTRKKKAL RIHSVEGDLR  180
RKSAGQEEWS PSAPSPPGSC VQAEAAPAGL CGEQRGEDCA ELHDYFNVLS YRSLGNCSFF  240
TETG                                                              244

SEQ ID NO: 32          moltype = AA  length = 32
FEATURE                Location/Qualifiers
source                 1..32
                       mol_type = protein
                       organism = synthetic construct
VARIANT                27
                       note = G or Q
SEQUENCE: 32
GVPDRFSGSG SGTDFTLKIS RVEAEDXGVY YC                                32

SEQ ID NO: 33          moltype = AA  length = 10
FEATURE                Location/Qualifiers
source                 1..10
                       mol_type = protein
                       organism = synthetic construct
VARIANT                3
                       note = G or Q
SEQUENCE: 33
FGXGTKLTAK                                                         10

SEQ ID NO: 34          moltype = AA  length = 32
FEATURE                Location/Qualifiers
source                 1..32
                       mol_type = protein
                       organism = synthetic construct
VARIANT                27
                       note = F or E
SEQUENCE: 34
GVPARFSGSG SGTSYTLTIS RLEPEDXAVY YC                                32

SEQ ID NO: 35          moltype = AA  length = 11
FEATURE                Location/Qualifiers
source                 1..11
                       mol_type = protein
                       organism = synthetic construct
SEQUENCE: 35
FGAGTKLTAK R                                                       11

SEQ ID NO: 36          moltype = AA  length = 23
FEATURE                Location/Qualifiers
source                 1..23
                       mol_type = protein
                       organism = synthetic construct
SEQUENCE: 36
DIVMTQTPLS LPVTPGEPAS ISC                                          23

SEQ ID NO: 37          moltype = AA  length = 15
FEATURE                Location/Qualifiers
source                 1..15
                       mol_type = protein
                       organism = synthetic construct
SEQUENCE: 37
WYLQKPGQSP QLLIY                                                   15

SEQ ID NO: 38          moltype = AA  length = 23
FEATURE                Location/Qualifiers
source                 1..23
                       mol_type = protein
```

-continued

```
                       organism = synthetic construct
SEQUENCE: 38
EIVLTQSPGT LSLSPGERAT MTC                                          23

SEQ ID NO: 39          moltype = AA  length = 15
FEATURE                Location/Qualifiers
source                 1..15
                       mol_type = protein
                       organism = synthetic construct
SEQUENCE: 39
WYQQKPGASP KLLIY                                                   15
```

SINGLE-CHAIN FRAGMENT VARIABLE COMPRISING MUTANT LIGHT CHAIN FRAMEWORK REGION

RELATED APPLICATIONS AND INCORPORATION BY REFERENCE

This application claims priority to Chinese Patent Application No. 202210463614.8 filed on Apr. 28, 2022.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing XML labeled "55556-00100SequenceListingXML" which was created on Apr. 18, 2023 and is 47 bytes. The entire content of the sequence listing is incorporated herein by reference in its entirety.

FIELD OF THE INVENTION

The application relates to a single-chain fragment variable (scFv) comprising a heavy chain variable region, a linker, and a κ light chain variable region, wherein the κ light chain variable region is engineered to comprise 104-106LTA, 83E, 83E/104-106LTA, 100Q/104-106LTA, or 83E/100Q/104-106LTA mutations according to the Kabat antibody numbering scheme. The scFv of the disclosure has improved conformational stability, higher expression level, and/or lower aggregation level.

BACKGROUND OF THE INVENTION

Naturally occurring antibody molecules found in animal bodies usually consist of two heavy chains and two light chains. Each heavy chain comprises a heavy chain variable region (VH) and a heavy chain constant region (CH), and each light chain comprises a light chain variable region (VL) and a light chain constant region (CL). The VH and the VL pair to form an antigen binding domain, while the CH (especially CH1) and the CL support the antigen binding domain's conformational stability. Such whole antibody molecules, including the anti-PD-1 Nivolumab and the anti-PD-L1 Atezolizumab, were the first type of antibody that were approved for clinical treatments.

With the development of the antibody technology, the scientists designed and prepared some small sized antibody fragments, such as the single-chain fragment variable (scFv). These molecules, as a result of the small size, exhibit some improved properties. For example, they can penetrate tissues inaccessible to normal full-length antibodies, have shorter half-life, and can be used to construct functional bispecific or multi-specific molecules as well as chimeric antigen receptors. However, despite the good bioactivity of many scFv-based molecules in therapeutic studies, the low expression level and the activity attenuation during storage do limit their applications in pre-clinical and clinical researches. Very few therapeutic scFv antibodies have been approved for marketing since scFv was discovered around 1990.

A scFv molecule usually consists of a VH, a VL, and a linker therebetween, having the N-terminus of the VH linked to the C-terminus of the VL, or the N-terminus of the VL linked to the C-terminus of the VH. The linker is typically a short peptide of 15 to 25 amino acid residues with certain flexibility, which enables formation of a monovalent antigen binding domain by the folded VH and VL. Probably due to the lack of support from the CH1 and CL, the VH and the VL in some scFvs cannot well interact and therefore form an unstable conformation that is between the VH-VL separation state and close VH-VL binding state. For example, due to the lack of CH1 and CL, some amino acid residues (such as a hydrophobic residue, or a residue for glycosylation) in the VH and the VL may be exposed at the surface, affecting the scFv's conformational stability and expression level. The lack of the CH1 and/or CL may also alter the charges at the surface of the VH and/or the VL which may also affect the VH-VL's conformational stability. With the accumulation of scFvs without close VH-VL pairing, the VH in one scFv may interact with the VL in another scFv, causing scFv aggregation, and the scFv aggregate may be stored in certain parts within the cells, leading to a low expression level. The scFvs that are secreted from the cells and tend to aggregate may cause the off-target effect during the clinical uses, which is the main problem for the scFv therapeutics. First of all, the antibody aggregation may adversely affect the antigen binding specificity. In the case of the anti-CD3 antibodies, since these antibodies initiate the CD3 signaling in the cross-linking status, in order to avoid unnecessary T cell activation, a bispecific antibody is commonly designed to target CD3 and a disease associated antigen and only induce CD3 signal transduction when the bispecific antibody binds the disease associated antigen to enable antibody cross-linking. If the bispecific antibodies are cross-linked at a non-target location due to the scFv aggregation, unspecific T cell reactions will be triggered, leading to severe cytokine release syndrome (CRS), lowering their clinical application value. Secondly, the antibody aggregation may induce immune responses by the hosts, generating antibodies against the antibody aggregates, which may accelerate antibody clearance and reduce efficacy (Joubert et al., (2012) *J. Biol. Chem.* 287(30):25266-25279). Plus, the removal of antibody aggregates during production may decrease production efficiency and increase cost (Cromwell et al., (2006) *AAPS Journal* 8(3): E572_E579).

In sum, the scFv molecules are likely to degrade and aggregate, with conformational instability and low production levels. There is a need for a method to improve the physical stability of an antibody or an antigen binding fragment, such as an scFv molecule, that is lack of the support from the constant region(s). Such a method may promote the development of next-generation therapeutic antibodies.

Citation or identification of any document in this application is not an admission that such a document is available as prior art to the present disclosure.

SUMMARY OF THE INVENTION

The present inventors, by comparing the Fab and scFv forms of a same antibody (see FIG. 1A to 1C), found that, some hydrophobic amino acid residues may be present in the third and fourth framework (FR) regions of the light chain (such as the κ light chain), especially the fourth framework region, and exposed at the surface when there is no support from the light chain constant region, resulting in an unstable antigen binding domain conformation. The VH-VL conformational stability may be improved by replacing the hydrophobic amino acid residue(s) with the hydrophilic or less hydrophobic amino acid residue(s), such that the scFv's aggregation propensity, the expression level and the storage stability may be improved. In addition, the amino acid residue(s) in the third and fourth framework (FR) regions of the light chain (such as the κ light chain), especially the fourth framework region, can be altered to improve the overall charge distribution, further elevating the conformational stability of the antibody binding domain formed by the VH and the VL. The modification mentioned above in the light chain framework regions may be also applicable to other constant region-lacking antibodies or antigen binding fragments, for conformational stability improvement.

Therefore, in a first aspect, the disclosure provides a single-chain fragment variable (scFv) that may comprise a heavy chain variable region, a linker, and a κ light chain variable region, wherein the κ light chain variable region may comprise the light chain framework regions, wherein the light chain framework regions may comprise a first, a second, a third and a fourth framework regions. The κ light chain variable region may be engineered to comprise leucine (Leu, L) at Position 104, serine (Ser, S) or threonine (Thr, T) at Position 105, and/or alanine (Ala, A), serine (Ser, S) or threonine (Thr, T) at Position 106, according to the Kabat numbering scheme. Positions 104 to 106 may be located in the fourth framework region of the κ light chain variable region, according to the Kabat numbering scheme.

In certain embodiments, the κ light chain variable region may be engineered to comprise threonine (Thr, T) at Position 105 according to the Kabat numbering scheme.

In certain embodiments, the κ light chain variable region may be engineered to comprise alanine (Ala, A) at Position 106 according to the Kabat numbering scheme.

In certain embodiments, the κ light chain variable region may be engineered to comprise leucine (Leu, L), threonine (Thr, T) and alanine (Ala, A) at Position 104 to 106, respectively, according to the Kabat numbering scheme.

The light chain variable region may be engineered to comprise glutamine (Gln, Q) at Position 100 according to the Kabat numbering scheme. Position 100 may be located at the fourth framework region of the κ light chain variable region according to the Kabat numbering scheme.

The light chain variable region may be engineered to comprise glutamic acid (Glu, E) at Position 83 according to the Kabat numbering scheme. Position 83 may be located at the third framework region of the κ light chain variable region according to the Kabat numbering scheme.

The light chain variable region may be engineered to comprise one or more amino acid residues selected from the group consisting of 83E, 100Q, 104L, 105T and 106A, according to the Kabat numbering scheme.

In certain embodiments, the light chain variable region may be engineered to comprise glutamic acid (Glu, E) at Position 83 according to the Kabat numbering scheme.

In certain embodiments, the light chain variable region may be engineered to comprise glutamine (Gln, Q), leucine (Leu, L), threonine (Thr, T) and alanine (Ala, A) at Position 100 and Position 104 to 106, respectively, according to the Kabat numbering scheme.

In certain embodiments, the light chain variable region may be engineered to comprise glutamic acid (Glu, E), leucine (Leu, L), threonine (Thr, T) and alanine (Ala, A) at Position 83 and 104 to 106, respectively, according to the Kabat numbering scheme.

In certain embodiments, the light chain variable region may be engineered to comprise glutamic acid (Glu, E), glutamine (Gln, Q), leucine (Leu, L), threonine (Thr, T) and alanine (Ala, A) at Position 83, 100 and 104 to 106, respectively, according to the Kabat numbering scheme.

The light chain variable region of the scFv of the disclosure may be also defined by another numbering scheme such as Chothia, IMGT, AbM or Contact, as long as Position 83, 100, and 104 to 106 are the same with those defined by the Kabat numbering scheme.

The light chain framework regions of the scFv of the disclosure may be those from the naturally occurring κ light chain (such as human κ light chain), or those having been engineered on the basis of the naturally occurring κ light chain (such as human κ light chain). The κ light chain may be the scFv scaffold FW1.4gen, 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, 43-FW1.4opt, or the above scaffold with one or more (e.g., 1 to 5) amino acid mutations at the first, second, third and/or fourth framework regions.

In one embodiment, the light chain variable region may comprise the framework regions (including the first, second, third and fourth framework regions) of the scFv scaffold FW1.4gen, 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, 43-FW1.4opt, or the above scaffold with one or more (e.g., 1 to 5) amino acid mutations at the first, second, third and/or fourth framework regions, wherein Position 104 to 106, according to the Kabat numbering scheme, may comprise leucine (Leu, L), threonine (Thr, T), and alanine (Ala, A), respectively, via e.g., mutation.

In one embodiment, the light chain variable region may comprise the framework regions (including the first, second, third and fourth framework regions) of the scFv scaffold FW1.4gen, 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, 43-FW1.4opt, or the above scaffold with one or more (e.g., 1 to 5) amino acid mutations at the first, second, third and/or fourth framework regions, wherein Position 100 and 104 to 106, according to the Kabat numbering scheme, may comprise glutamine (Gln, Q), leucine (Leu, L), threonine (Thr, T), and alanine (Ala, A), respectively, via e.g., mutation; Position 83 may comprise glutamic acid (Glu, E), via e.g., mutation; Position 83 and 104 to 106 may comprise glutamic acid (Glu, E), leucine (Leu, L), threonine (Thr, T), and alanine (Ala, A), respectively, via e.g., mutation; or Position 83, 100 and 104 to 106 may comprise glutamic acid (Glu, E), glutamine (Gln, Q), leucine (Leu, L), threonine (Thr, T), and alanine (Ala, A), respectively, via e.g., mutation.

The light chain variable region of the scFv of the disclosure may comprise a fourth framework region comprising 104-106LTA, such as a fourth framework region comprising the amino acid sequence of SEQ ID NOs: 33 (X=G) or 35.

Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise a third framework region comprising 83E, and/or a fourth framework region comprising 104-106LTA or 100Q/104-106LTA, such as a third framework region comprising the amino acid sequence of SEQ ID NOs: 32 (X=E) or 34 (X=E), and/or a fourth framework region comprising the amino acid sequence of SEQ ID NOs: 33 (X=G or Q) or 35. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

In certain embodiments, the light chain variable region of the scFv of the disclosure may comprise a first framework region, a second framework region, a third framework region with 83E, and a fourth framework region with 104-106LTA or 100Q/104-106LTA, such as the third framework region of SEQ ID NO: 32 (X=E), and the fourth framework region of SEQ ID NO: 33 (X=G or Q). In one embodiment, the light chain variable region of the scFv of the disclosure may comprise a first framework region, a second framework region, a third framework region with 83E, and a fourth framework region with 104-106LTA, such as the third framework region of SEQ ID NO: 34 (X=E), and the fourth framework region of SEQ ID NO: 35. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the fourth framework region, or the first to fourth framework regions from the light chain variable region comprising the amino acid sequence of SEQ ID NOs: 16 (X1=V, X2=G, X3=L, X4=T, X5=A; X1=E, X2=G, X3=V, X4=E, X5=I; or X1=E, X2=Q, X3=L, X4=T, X5=A) or 24 (X1=E, X2=T, X3=A). The light chain variable region may comprise the third and fourth framework regions, or the first to fourth framework regions from the light chain variable region comprising the amino acid sequence of SEQ ID NOs: 16 (X1=V, X2=G, X3=L, X4=T, X5=A; X1=E, X2=G, X3=V, X4=E, X5=I; or X1=E, X2=Q, X3=L, X4=T, X5=A) or 24 (X1=E, X2=T, X3=A). The light chain variable region may comprise the first, second, third and fourth framework regions from the light chain variable region comprising the amino acid sequence of SEQ ID NOs: 16 (X1=V, X2=G, X3=L, X4=T, X5=A; X1=E, X2=G, X3=V, X4=E, X5=I; or X1=E, X2=Q, X3=L, X4=T, X5=A) or 24 (X1=E, X2=T, X3=A). Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the first, second, third and fourth framework regions comprising the amino acid sequences of SEQ ID NOs: 36, 37, 32 (X=V or E), and 33 (X=G or Q), respectively. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the first, second, third and fourth framework regions comprising the amino acid sequences of SEQ ID NOs: 38, 39, 34 (X=F or E), and 35, respectively. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

In one embodiment, the scFv of the disclosure may bind CD20 or TIGIT.

The linker in the scFv of the disclosure may be a short peptide of 10 to 25 amino acid residues, such as a GS linker, e.g., -$(G_4S)_3$- (SEQ ID NO: 27), -$(G_4S)_4$- (SEQ ID NO: 28), and -$(G_4S)_5$- (SEQ ID NO: 29).

In a second aspect, the present disclosure provides an antibody or an antigen binding fragment that may comprise the scFv of the disclosure.

The antibody or antigen binding fragment may be a scFv. The antibody or antigen binding fragment may be a bispecific or multi-specific antibody.

In one embodiment, the antibody or antigen binding fragment may be a scFv targeting CD20, comprising a heavy chain variable region, a linker, and a light chain variable region, wherein the light chain variable region is a κ light chain variable region, wherein the heavy chain variable region comprises a heavy chain variable region CDR1 (VH-CDR1), a VH-CDR2 and a VH-CDR3 comprising the amino acid sequences of SEQ ID NOs: 7, 8 and 9, respectively, and the light chain variable region comprises a light chain variable region CDR1 (VL-CDR1), a VL-CDR2 and a VL-CDR3 comprising the amino acid sequences of SEQ ID NOs: 10, 11 and 12, respectively, wherein the light chain variable region further comprises a first, second, third and fourth framework regions, wherein the light chain variable region comprises leucine (Leu, L) at Position 104, serine (Ser, S) or threonine (Thr, T) at Position 105, alanine (Ala, A), serine (Ser, S) or threonine (Thr, T) at Position 106, according to the Kabat numbering scheme. In certain embodiments, the light chain variable region may comprise leucine (Leu, L), threonine (Thr, T), and alanine (Ala, A) at Position 104 to 106, according to the Kabat numbering scheme. According to the Kabat numbering scheme, the light chain variable region may comprise glutamine (Gln, Q) at Position 100. According to the Kabat numbering scheme, the light chain variable region may comprise glutamic acid (Glu, E) at Position 83. In certain embodiments, the light chain variable region may comprise a fourth framework region with 104-106LTA, or 100Q/104-106LTA, such as a fourth framework region of SEQ ID NO: 33 (X=G or Q). In certain embodiments, the light chain variable region may comprise a third framework region with 83E, such as a third framework region of SEQ ID NO: 32 (X=E). In certain embodiments, the light chain variable region may comprise a third framework region with 83V or 83E, and a fourth framework region with 104-106LTA or 100Q/104-106LTA, such as a third framework region of SEQ ID NO: 32 (X=V or E) and a fourth framework region of SEQ ID NO: 33 (X=G or Q). In certain embodiments, the light chain variable region may comprise the amino acid residue 83E, 104-106LTA, 83E/104-106LTA, 100Q/104-106LTA, or 83E/

100Q/104-106TLA, e.g., the amino acid sequence of SEQ ID NO: 16 (X1=V, X2=G, X3=L, X4=T, X5=A; X1=E, X2=G, X3=V, X4=E, X5=I; or X1=E, X2=Q, X3=L, X4=T, X5=A). In one embodiment, the scFv may comprise a heavy chain variable region, a linker, and a light chain variable region, wherein the heavy chain variable region comprises the amino acid sequence of SEQ ID NO: 15, the linker comprises the amino acid sequence of SEQ ID NOs: 27, 28 or 29, and the light chain comprises the amino acid residue 83E, 104-106LTA, 83E/104-106LTA, 100Q/104-106LTA, or 83E/100Q/104-106TLA, and the amino acid sequence of e.g., SEQ ID NO: 16 (X1=V, X2=G, X3=L, X4=T, X5=A; X1=E, X2=G, X3=V, X4=E, X5=I; or X1=E, X2=Q, X3=L, X4=T, X5=A). In one embodiment, the scFv, from N-terminus to C-terminus, comprises a heavy chain variable region, a linker, and a light chain variable region, wherein the heavy chain variable region comprises the amino acid sequence of SEQ ID NO: 15, the linker comprises the amino acid sequence of SEQ ID NOs: 27, 28 or 29, and the light chain comprises the amino acid residue 83E, 104-106LTA, 83E/104-106LTA, 100Q/104-106LTA, or 83E/100Q/104-106TLA, and the amino acid sequence of e.g., SEQ ID NO: 16 (X1=V, X2=G, X3=L, X4=T, X5=A; X1=E, X2=G, X3=V, X4=E, X5=I; or X1=E, X2=Q, X3=L, X4=T, X5=A).

In certain embodiments, the antibody or antigen binding fragment may be a bispecific antibody targeting CD20 and CD3, which may comprise one anti-CD3E antigen binding domain, and one to five anti-CD20 antigen binding domains. The anti-CD3 antigen binding domain may be in the Fab, Fv or scFv format, and the anti-CD20 antigen binding domain may be in the Fab, Fv or scFv format. At least one anti-CD20 antigen binding domain may be in the scFv format, and may be the scFv described above that targets CD20.

The bispecific antibody may comprise a Fab specifically binding CD3, a Fab specifically binding CD20, and a scFv specifically binding CD20. The scFv specifically binding CD20 may be the scFv containing the engineered light chain framework regions of the disclosure, i.e., the light chain variable region may comprise the amino acid residue 83E, 104-106LTA, 83E/104-106LTA, 100Q/104-106LTA, or 83E/100Q/104-106LTA.

The Fab specifically binding CD3 may comprise a heavy chain variable region CDR1 (VH-CDR1), a VH-CDR2, a VH-CDR3, a light chain variable region CDR1 (VL-CDR1), a VL-CDR2 and a VL-CDR3 comprising the amino acid sequences of SEQ ID NOs: 1, 2, 3, 4, 5 and 6, respectively. The Fab specifically binding CD20 and the scFv specifically binding CD20 may comprise a VH-CDR1, a VH-CDR2, a VH-CDR3, a VL-CDR1, a VL-CDR2 and a VL-CDR3 comprising the amino acid sequences of SEQ ID NOs: 7, 8, 9, 10, 11 and 12, respectively.

The Fab specifically binding CD3 may comprise a heavy chain variable region comprising an amino acid sequence having at least 90%, 91%, 92%, 93%, 94%, 95%, 96%, 97%, 98%, 99% or 100% sequence identity to SEQ ID NO: 13, and a light chain variable region comprising an amino acid sequence having at least 90%, 91%, 92%, 93%, 94%, 95%, 96%, 97%, 98%, 99% or 100% sequence identity to SEQ ID NO: 14. The Fab specifically binding CD20 may comprise a heavy chain variable region comprising an amino acid sequence having at least 90%, 91%, 92%, 93%, 94%, 95%, 96%, 97%, 98%, 99% or 100% sequence identity to SEQ ID NO: 15, and a light chain variable region comprising an amino acid sequence having at least 90%, 91%, 92%, 93%, 94%, 95%, 96%, 97%, 98%, 99% or 100% sequence identity to SEQ ID NO: 16 (X1=V, X2=G, X3=V, X4=E, X5=I). The scFv specifically binding CD20 may comprise a heavy chain variable region comprising an amino acid sequence having at least 90%, 91%, 92%, 93%, 94%, 95%, 96%, 97%, 98%, 99% or 100% sequence identity to SEQ ID NO: 15, and a light chain variable region comprising an amino acid sequence having at least 90%, 910%, 92%, 93%, 94%, 95%, 96%, 97%, 98%, 99% or 100% sequence identity to SEQ ID NO: 16 (X1=V, X2=G, X3=L, X4=T, X5=A; X1=E, X2=G, X3=V, X4=E, X5=I; or X1=E, X2=Q, X3=L, X4=T, X5=A).

The bispecific antibody of the disclosure may comprise:

i) a first polypeptide chain, comprising (optionally from N-terminus to C-terminus) an anti-CD20 heavy chain variable region, and a heavy chain constant region CH1-CH2-CH3;

ii) a second polypeptide chain, comprising (optionally from N-terminus to C-terminus) an anti-CD20 light chain variable region, and a light chain constant region;

iii) a third polypeptide chain, comprising (optionally from N-terminus to C-terminus) an anti-CD20 heavy chain variable region, an anti-CD20 light chain variable region, an anti-CD3E heavy chain variable region, and a heavy chain constant region CH1-CH2-CH3; and iv) a fourth polypeptide chain, comprising (optionally from N-terminus to C-terminus) an anti-CD3ε light chain variable region and a light chain constant region, wherein the anti-CD20 heavy chain variable region and the heavy chain constant region CH1 in the first polypeptide chain may associate with the anti-CD20 light chain variable region and the light chain constant region in the second polypeptide chain to form an anti-CD20 Fab, the anti-CD20 heavy chain variable region and the anti-CD20 light chain variable region in the third polypeptide chain may associate to form an anti-CD20 scFv, the anti-CD3ε heavy chain variable region and the heavy chain constant region CH1 in the third polypeptide chain may associate with the anti-CD3ε light chain variable region and the light chain constant region in the fourth polypeptide chain to form an anti-CD3 Fab, and the heavy chain constant region in the first polypeptide chain and the constant region in the third polypeptide chain are bonded covalently, or via e.g., the knobs-into-holes technology, or the disulfide bond(s).

The heavy chain constant regions in the first and third polypeptide chains may have reduced or eliminated FcR binding activity, with one with knob mutation(s) and the other with hole mutation(s).

In one embodiment, the heavy chain constant region in the first polypeptide chain may be an IgG1 heavy chain constant region with L234A/L235A/N297A/T366W mutations, and the heavy chain constant region in the third polypeptide chain may be an IgG1 heavy chain constant region with L234A/L235A/N297A/T366S/L368A/Y407V mutations; or alternatively, the heavy chain constant region in the first polypeptide chain may be an IgG1 heavy chain constant region with L234A/L235A/N297A/T366S/L368A/Y407V mutations, and the heavy chain constant region in the third polypeptide chain may be an IgG1 heavy chain constant region with L234A/L235A/N297A/T366W mutations.

In one embodiment, the bispecific antibody of the disclosure may comprise:

i) a first polypeptide chain, comprising an anti-CD20 heavy chain variable region, and a heavy chain constant region;

ii) a second polypeptide chain, comprising an anti-CD20 light chain variable region;

iii) a third polypeptide chain, comprising an anti-CD20 heavy chain variable region, an anti-CD20 light chain variable region, an anti-CD3ε heavy chain variable region, and a heavy chain constant region; and iv) a fourth polypeptide chain, comprising an anti-CD3ε light chain variable region, wherein the anti-CD20 light chain variable region in the first polypeptide chain may associate with the anti-CD20 light chain variable region in the second polypeptide chain to form an anti-CD20 antigen binding fragment, the anti-CD20 heavy chain variable region and the anti-CD20 light chain variable region in the third polypeptide chain may associate to form an anti-CD20 antigen binding fragment, the anti-CD3ε heavy chain variable region in the third polypeptide chain may associate with the anti-CD3ε light chain variable region in the fourth polypeptide chain to form an anti-CD3 antigen binding fragment, and the heavy chain constant region in the first polypeptide chain and the constant region in the third polypeptide chain are bonded covalently, or via e.g., the knobs-into-holes technology, or the disulfide bond(s).

The anti-CD20 heavy chain variable region in the first and third polypeptide chains may comprise a VH-CDR1, a VH-CDR2 and a VH-CDR3 comprising the amino acid sequences of SEQ ID NOs: 7, 8 and 9. In one embodiment, the anti-CD20 heavy chain variable region in the first and third polypeptide chains may comprise an amino acid sequence having at least 90%, 91%, 92%, 93%, 94%, 95%, 96%, 97%, 98%, 99% or 100% sequence identity to SEQ ID NO: 15.

The anti-CD20 light chain variable region in the second and third polypeptide chains may comprise a VL-CDR1, a VL-CDR2 and a VL-CDR3 comprising the amino acid sequences of SEQ ID NOs: 10, 11 and 12. The anti-CD20 light chain variable region in the third polypeptide chain, may comprise amino acid residue 83E, 104-106LTA, 83E/104-106LTA, 100Q/104-106LTA, or 83E/100Q/104-106LTA according to the Kabat numbering scheme. In one embodiment, the anti-CD20 light chain variable region in the third polypeptide chain may comprise an amino acid sequence having at least 90%, 91%, 92%, 93%, 94%, 95%, 96%, 97%, 98%, 99% or 100% sequence identity to SEQ ID NO: 16 (X1=V, X2=G, X3=L, X4=T, X5=A; X1=E, X2=G, X3=V, X4=E, X5=I; or X1=E, X2=Q, X3=L, X4=T, X5=A). The anti-CD20 light chain variable region in the second polypeptide chain may comprise wildtype framework regions, or engineered framework regions with 83E, 104-106LTA, 83E/104-106LTA, 100Q/104-106LTA, or 83E/100Q/104-106LTA. In one embodiment, the anti-CD20 light chain variable region in the second polypeptide chain may comprise a naturally occurring κ light chain without amino acid mutation at Position 83, 100, 104, 105 or 106. In one embodiment, the anti-CD20 light chain variable region in the second polypeptide chain may comprise an amino acid sequence having at least 90%, 91%, 92%, 93%, 94%, 95%, 96%, 97%, 98%, 99% or 100% sequence identity to SEQ ID NO: 16 (X1=V, X2=G, X3=V, X4=E, X5=I).

The anti-CD3ε heavy chain variable region in the third polypeptide chain may comprise a VH-CDR1, a VH-CDR2 and a VH-CDR3 comprising the amino acid sequences of SEQ ID NOs: 1, 2 and 3, respectively. In one embodiment, the anti-CD3ε heavy chain variable region in the third polypeptide chain may comprise an amino acid sequence having at least 90%, 91%, 92%, 93%, 94%, 95%, 96%, 97%, 98%, 99% or 100% sequence identity to SEQ ID NO: 13.

The anti-CD3ε light chain variable region in the fourth polypeptide chain may comprise a VL-CDR1, a VL-CDR2 and a VL-CDR3 comprising the amino acid sequences of SEQ ID NOs: 4, 5 and 6, respectively. In one embodiment, the anti-CD3ε light chain variable region in the fourth polypeptide chain may comprise an amino acid sequence having at least 90%, 91%, 92%, 93%, 94%, 95%, 96%, 97%, 98%, 99% or 100% sequence identity to SEQ ID NO: 14.

The heavy chain constant region in the first polypeptide chain may be a knob variant, such as a human IgG1 heavy chain constant region or a functional fragment thereof with T366W. The heavy chain constant region in the first polypeptide chain may be a knob variant with weak or no FcR binding affinity, such as human IgG1 heavy chain constant region comprising the amino acid sequence of SEQ ID NO: 19 (X1=W, X2=L, X3=Y). The heavy chain constant region in the third polypeptide chain may be a hole variant, such as human IgG1 heavy chain constant region or a functional fragment with T366S/L368A/Y407V. The heavy chain constant region in the third polypeptide chain may be a hole variant with weak or no FcR binding affinity, such as human IgG1 heavy chain constant region comprising the amino acid sequence of SEQ ID NO: 19 (X1=S, X2=A, X3=V).

Alternatively, the heavy chain constant region in the first polypeptide chain may be a hole variant, such as a human IgG1 heavy chain constant region or a functional fragment thereof with T366S/L368A/Y407V. The heavy chain constant region in the first polypeptide chain may be a hole variant with weak or no FcR binding affinity, such as human IgG1 heavy chain constant region comprising the amino acid sequence of SEQ ID NO: 19 (X1=S, X2=A, X3=V). The heavy chain constant region in the third polypeptide chain may be a knob variant, such as human IgG1 heavy chain constant region or a functional fragment with T366W. The heavy chain constant region in the third polypeptide chain may a knob variant with weak or no FcR binding affinity, such as human IgG1 heavy chain constant region comprising the amino acid sequence of SEQ ID NO: 19 (X1=W, X2=L, X3=Y).

The anti-CD20 heavy chain variable region in the third polypeptide chain may be linked to the anti-CD20 light chain variable region with a linker. In one embodiment, the linker may be a peptide of about 15 to 30 amino acid residues. In one embodiment, the linker may be a GS linker, such as a GS linker comprising the amino acid sequence of SEQ ID NOs: 27, 28 or 29.

In the third polypeptide chain, the anti-CD20 light chain variable region or the anti-CD20 heavy chain variable region may be linked to the anti-CD3ε heavy chain variable region or the heavy chain constant region via a linker. In one embodiment, the linker may be a peptide of about 15 to 30 amino acid residues. In one embodiment, the linker may be a GS linker, such as a GS linker comprising the amino acid sequence of SEQ ID NOs: 27, 28 or 29.

The first polypeptide chain may comprise, from N-terminus to C-terminus, the anti-CD20 heavy chain variable region and the heavy chain constant region.

The third polypeptide chain may comprise, from N-terminus to C-terminus, the anti-CD20 heavy chain variable region, the anti-CD20 light chain variable region, the anti-CD3ε heavy chain variable region, and the heavy chain constant region; the anti-CD20 light chain variable region, the anti-CD20 heavy chain variable region, the anti-CD3ε heavy chain variable region, and the heavy chain constant region; the anti-CD3ε heavy chain variable region, the heavy chain constant region, the anti-CD20 heavy chain variable region, and the anti-CD20 light chain variable region; or the anti-CD3ε heavy chain variable region, the heavy chain constant region, the anti-CD20 light chain variable region, and the anti-CD20 heavy chain constant region.

The second polypeptide chain may further comprise a light chain constant region at the C-terminus, such as a light chain constant region of SEQ ID NO: 18.

The fourth polypeptide chain may further comprise a light chain constant region at the C-terminus, such as a light chain constant region of SEQ ID NO: 17.

In one embodiment, the first polypeptide chain may comprise, from N-terminus to C-terminus, the anti-CD20 heavy chain variable region and the heavy chain constant region, wherein the heavy chain constant region may a hole variant; the second polypeptide chain may comprise, from N-terminus to C-terminus, the anti-CD20 light chain variable region and the light chain constant region; the third polypeptide chain may comprise, from N-terminus to C-terminus, the anti-CD20 heavy chain variable region, a linker, the anti-CD20 light chain variable region, a linker, the anti-CD3ε heavy chain variable region, and the heavy chain constant region, wherein the heavy chain constant region may be a knob variant; the fourth polypeptide chain may comprise, from N-terminus to C-terminus, the anti-CD3ε light chain variable region and the light chain constant region. In one embodiment, the first, second, third and fourth polypeptide chains may comprise the amino acid sequences of SEQ ID NOs: 21, 23, 20 (X1=E, X2=Q, X3=L, X4=T, X5=A; X1=V, X2=G, X3=L, X4=T, X5=A; X1=E, X2=G, X3=V, X4=E, X5=I) (according to the Kabat numbering scheme, with 83E/100Q/104-106LTA, 83E, or 104-106LTA), and 22, respectively.

The bispecific antibody of the disclosure, in another embodiment, may comprise i) a first polypeptide chain, comprising an anti-CD20 heavy chain variable region, and a heavy chain constant region;

ii) a second polypeptide chain, comprising an anti-CD20 light chain variable region;

iii) a third polypeptide chain, comprising an anti-CD3ε heavy chain variable region and a heavy chain constant region;

iv) a fourth polypeptide chain, comprising an anti-CD20 heavy chain variable region, an anti-CD20 light chain variable region, and an anti-CD3c light chain variable region, wherein the anti-CD20 heavy chain variable region in the first polypeptide chain may associates with the anti-CD20 light chain variable region in the second polypeptide chain to form an anti-CD20 antigen binding fragment, the anti-CD3ε heavy chain variable region in the third polypeptide chain may associate with the anti-CD3ε light chain variable region in the fourth polypeptide chain to form an anti-CD3 antigen binding fragment, the anti-CD20 heavy chain variable region and the anti-CD20 light chain variable region in the fourth polypeptide chain may associate to form an anti-CD20 antigen binding fragment, and the heavy chain constant region in the first polypeptide chain and the heavy chain constant region in the third polypeptide chain are bonded covalently, or via e.g., the knobs-into-holes approach, or the disulfide bond(s).

The components in the first, second, third and fourth polypeptide chains are defined as above. The anti-CD20 light chain variable region in the fourth polypeptide chain may comprise amino acid residue 83E, 104-106LTA, 83E/104-106LTA, 100Q/104-106LTA, or 83E/100Q/104-106LTA.

In one embodiment, the first polypeptide chain may comprise, from N-terminus to C-terminus, the anti-CD20 heavy chain variable region, and the heavy chain constant region. The third polypeptide chain may comprise, from N-terminus to C-terminus, the anti-CD3ε heavy chain variable region and the heavy chain constant region. The fourth polypeptide chain may comprise, from N-terminus to C-terminus, the anti-CD20 heavy chain variable region, the anti-CD20 light chain variable region, and the anti-CD3ε light chain variable region; the anti-CD20 light chain variable region, the anti-CD20 heavy chain variable region and the anti-CD3ε light chain variable region; the anti-CD3ε light chain variable region, the anti-CD20 light chain variable region, and the anti-CD20 heavy chain variable region; or alternatively the anti-CD3ε light chain variable region, the anti-CD20 heavy chain variable region and the anti-CD20 light chain variable region.

The bispecific antibody may further comprise a light chain constant region at the C-terminus of the anti-CD20 light chain variable region, and/or a light chain constant region at the C-terminus of the anti-CD3ε light chain variable region.

In a third aspect, the disclosure provides a nucleic acid molecule encoding the antibody or antigen binding fragment of the disclosure, as well as an expression vector comprising such a nucleic acid molecule and a host cell comprising such an expression vector or having the nucleic acid molecule integrated into its genome. A method for preparing the antibody or antigen binding fragment using the host cell of the disclosure is provided, comprising steps of (i) expressing the antibody or antigen binding fragment in the host cell, and (ii) isolating the antibody or antigen binding fragment from the host cell or its cell culture.

In a fourth aspect, the disclosure provides a composition, e.g., a pharmaceutical composition, which may comprise the antibody or antigen binding fragment (including the bispecific antibody), the nucleic acid molecule, the expression vector or the host cell of the disclosure, and a pharmaceutically acceptable carrier.

In a fifth aspect, the disclosure provides a method for producing the antibody or antigen binding fragment, such as a scFv or a scFv-containing antibody, of the disclosure, comprising introducing a VL-CDR1, a VL-CDR2 and a VL-CDR3 of an antibody into the framework regions with 83E, 104-106LTA, 83E/104-106LTA, 100Q/104-106LTA, or 83E/100Q/104-106LTA, and expressing the resultant antibody or antigen binding fragment. In particular, the sequences encoding the VL-CDR1, VL-CDR2 and VL-CDR3 of the antibody are introduced into a coding sequence of framework regions, wherein according to the Kabat numbering scheme, the light chain variable region may be expressed to contain leucine (Leu, L) at Position 104, serine (Ser, S) or threonine (Thr, T) at Position 105, alanine (Ala, A), serine (Ser, S) or threonine (Thr, T) at Position 106, optionally glutamine (Gln, Q) at Position 100, and optionally glutamic acid (Glu, E) at Position 83. In certain embodiments, the amino acid residue at Position 105 may be threonine (Thr, T), according to the Kabat numbering scheme. In certain embodiments, the amino acid residue at Position 106 may be alanine (Ala, A), according to the Kabat numbering scheme. In one embodiment, the method may comprise: i) replacing the nucleotides in a nucleic acid construct encoding the amino acid residues at Position 104, 105 and 106 with those encoding leucine (Leu, L), serine (Ser, S)/threonine (Thr, T), and alanine (Ala, A)/serine (Ser, S)/threonine (Thr, T), respectively, optionally replacing the nucleotides encoding the amino acid residue at Position 100 with those encoding glutamine (Gln, Q), and optionally replacing the nucleotides encoding the amino acid residue at Position 83 with those encoding glutamic acid (Glu, E); ii)

optionally introducing the nucleotides coding for the VL-CDR1, VL-CDR2 and VL-CDR3 to the nucleic acid construct, and iii) expressing the antibody or antigen binding fragment in the nucleic acid construct under a suitable condition. In one embodiment, the method may comprise: i) replacing the nucleotides encoding the fourth framework region with those encoding SEQ ID NO: 33 (X=G or Q), optionally replacing the nucleotides encoding the third framework region with those encoding SEQ ID NO: 32 (X=E), and optionally replacing the nucleotides encoding the first and second framework regions with those encoding SEQ ID NOs: 36 and 37, respectively; or alternatively, replacing the nucleotides encoding the fourth framework region with those encoding SEQ ID NO: 35, optionally replacing the nucleotides encoding the third framework region with those encoding SEQ ID NO: 34 (X=E), and optionally replacing the nucleotides encoding the first and second framework regions with those encoding SEQ ID NOs: 38 and 39, respectively, in the nucleic acid construct (e.g., a recombinant vector) comprising the nucleic acid coding the light chain, ii) optionally introducing the nucleotides coding for the VL-CDR1, VL-CDR2 and VL-CDR3 to the nucleic acid construct, and iii) expressing the antibody or antigen binding fragment in the nucleic acid construct under a suitable condition. When the nucleic acid construct has been with the nucleotides encoding light chain CDRs, step ii) may be omitted. In one embodiment, the method may comprise: i) replacing the CDR-coding nucleotides with those encoding the antibody VL-CDR1, VL-CDR2 and VL-CDR3 in a nucleic acid construct (e.g., a recombinant vector) containing the nucleotides encoding SEQ ID NOs: 16 (X1=V, X2=G, X3=L, X4=T, X5=A; X1=E, X2=G, X3=V, X4=E, X5=I; X1=E, X2=Q, X3=L, X4=T, X5=A) or 24 (X1=E, X2=T, X3=A), and ii) expressing the antibody or antigen binding fragment in the nucleic acid construct under a suitable condition. Optionally, one or more (e.g., 1 to 5) amino acid mutations may be contained in the first, second and third framework regions. Optionally, one or more (e.g., 1 to 5) amino acid mutations may be contained in the first and second framework regions. The light chain variable region may be defined by another numbering scheme such as Chothia, IMGT, AbM or Contact, as long as Position 83, 100, and 104 to 106 are the same with those defined by the Kabat numbering scheme.

In a sixth aspect, the disclosure provides use of the anti-CD3/CD20 bispecific antibody of the disclosure or a functional fragment thereof in treatment or alleviation of a B cell associated disease in a subject in need thereof. In certain embodiments, the B cell associated disease is B-cell lymphoma, B-cell leukemia, or a B cell-mediated autoimmune disease. In certain embodiments, B-cell lymphoma and B-cell leukemia include, but not limited to, non-Hodgkin's lymphoma (NHL), chronic lymphocytic leukemia (CLL), and diffuse large B-cell lymphoma (DLBCL). In one embodiment, the subject may be administered with an anti-CD20 antibody before the administration of the bispecific molecule or functional fragment thereof of the disclosure.

When the light chain variable region framework region(s) in an antibody or an antigen binding fragment, especially those without the constant region(s), is/are engineered/modified to contain 83E, 104-106LTA, 83E/104-106LTA, 100Q/104-106LTA, or 83E/100Q/104-106LTA, according to the Kabat numbering scheme, the aggregation propensity and the stability (including thermal stability) can be significantly improved, and the expression level can be increased by 1 to 3 times, such as 1, 1.5, 1.9, 2.5, 2.9, or 3 times. In particular, the engineering or modification at the light chain variable region framework region(s) according to the present application may not affect the antigen binding affinity/activity and specificity of the antibody or antigen binding fragment.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the application not to encompass within the application any previously known product, process of making the product, or method of using the product such that Applicants reserve the right and hereby disclose a disclaimer of any previously known product, process, or method. It is further noted that the application does not intend to encompass within the scope of the application any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the application to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the application.

DESCRIPTION OF THE DRAWINGS

The following detailed description, given by way of example, but not intended to limit the application solely to the specific embodiments described, may best be understood in conjunction with the accompanying drawings.

DETAILED DESCRIPTION OF THE APPLICATION

Figure 1:
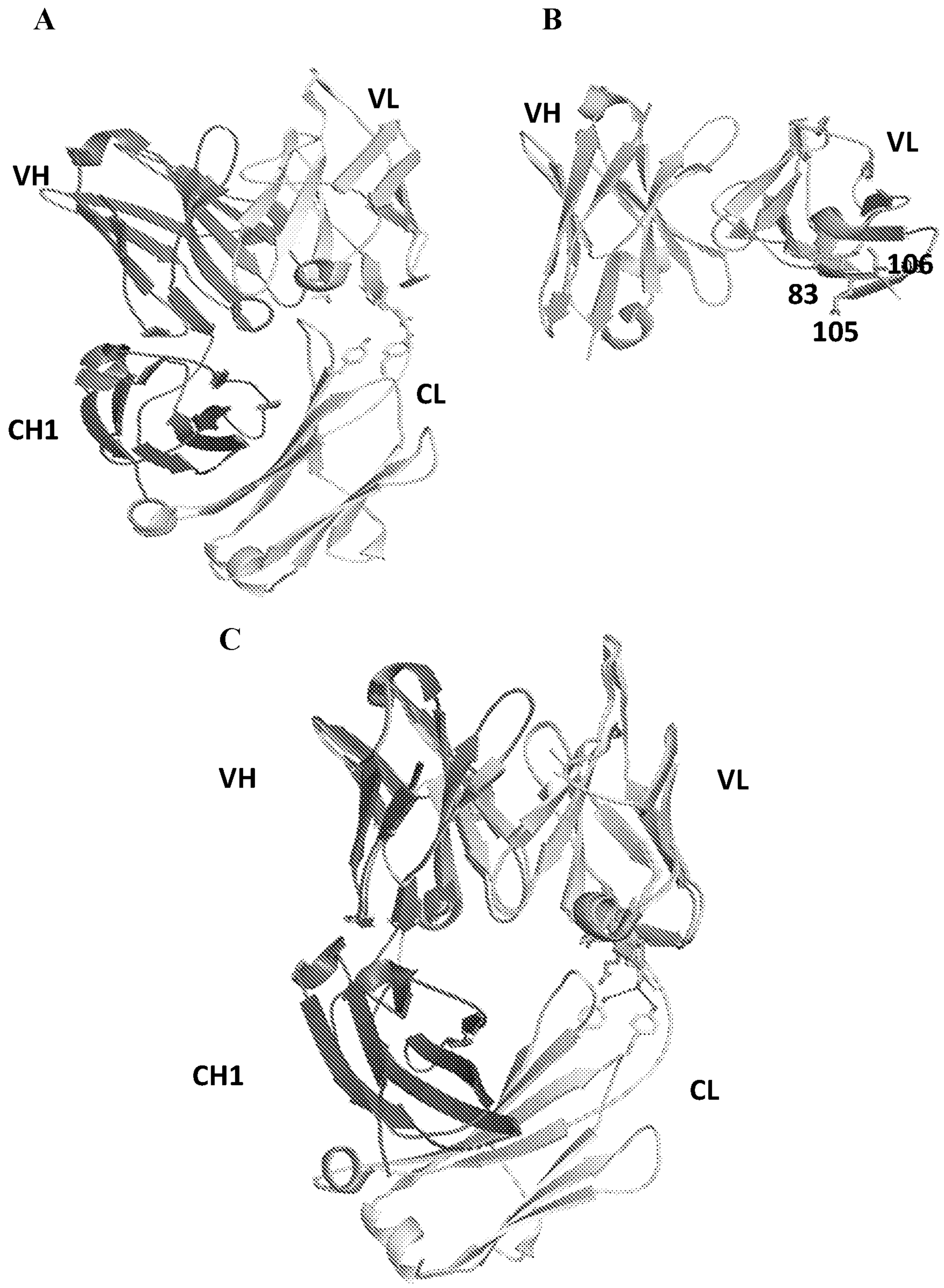
FIG. 1 shows the images of the Fab crystal conformation (A), the scFv crystal conformation (B), and superimposition of these two conformations (C) of an antibody in Pymol.

To ensure that the present disclosure may be more readily understood, certain terms are first defined. Additional definitions are set forth throughout the detailed description.

The term "antibody" as referred to herein includes whole antibodies of e.g., IgG, IgA, IgD, IgE and IgM, and any antigen binding fragment (i.e., "antigen-binding fragment") or single chains thereof. Whole antibodies are glycoproteins comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, $C_{H1}$, $C_{H2}$ and $C_{H3}$. Each light chain is comprised of a light chain variable region (abbreviated herein as VL) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each VH and V L is composed of three CDRs and four FRs, arranged from amino-terminus to carboxy-terminus in the following order: FR1, CDR1, FR2, CDR2, FR3, CDR3, FR4. The variable regions of the heavy and light chains comprise a binding domain that interacts with an antigen. The constant regions of the antibodies can mediate the binding of the immunoglobulin to host tissues or factors, including various cells of the immune system (e.g., effector cells) and the first component (C1q) of the classical complement system. A "functional fragment" of a heavy chain constant region refers to a part of the constant region that retains the capability to mediate binding of the immunoglobulin to host tissues or factors, including various cells of the immune system (e.g., effector cells) and the first component (C1q) of the classical complement system, to initiate e.g., ADCC, CDC, ADCP and the like.

The "knob variant" of a heavy chain constant region, or a heavy chain constant region with "knob mutation(s)" refers to a heavy chain constant region used in the knobs-into-holes technology whose CH3 domains are engineered to create a "knob". Similarly, the "hole variant" of a heavy chain constant region, or a heavy chain constant region with "hole mutation(s)" refers to a heavy chain constant region used in the knobs-into-holes technology whose CH3 domains are engineered to create a "hole".

The "bispecific" molecule refers to a molecule that specifically binds two target molecules, or two different epitopes on a target molecule, such as a bispecific antibody, including the bispecific molecules of the disclosure that specifically target CD3 and CD20, or TIGIT and VEGF, while the "monospecific" molecule refers to a molecule that specifically binds one target molecule, e.g., one epitope in a target molecule. The "functional fragment" of a bispecific molecule refers to the part of the bispecific molecule that retains the binding affinity to target(s) (e.g., CD3 and CD20, or TIGIT and VEGF), optionally the binding affinity to FcRs, and other required characteristics.

The term "half antibody" or "half-antibody" refers to one half of an antibody which comprises e.g., a heavy chain and a light chain.

The term "antigen-binding fragment" of an antibody (or simply "antibody portion"), as used herein, refers to one or more fragments of an antibody that retain the ability to specifically bind to an antigen (e.g., a CD20 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a VH domain; (vi) an isolated complementarity determining region (CDR); and (viii) a nanobody, a heavy chain variable region comprising a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "FcR" refers to a kind of molecule that is found on the surface of certain cells and can be bound by the Fc regions of the immunoglobulins. One type of the FcR is present on effector cells, including B lymphocytes, natural killing cells, and macrophages, that may induce phagocytosis of or cytotoxicity to target cells and play an important role in immunity, including the Fcα, Fcε and Fcγ receptors. The Fcγ receptor, as a member of the immunoglobulin superfamily, is the most important Fc receptor that is involved in the phagocytosis of microorganisms, including FcγRI (FcgRIa, CD64), FcγRIIA (FcgRIIa, CD32A), FcγRIIB (FcgRIIa, CD32B), and FcγRIIIA (FcgRIIIa, CD16A). Another type of the FcR includes polymeric immunoglobulin receptor and neonatal Fc receptor (FcRn). The FcRn, mainly expressed by the endothelial cells with a structure similar to the MHC-I molecule, is involved in the translocation, maintenance and distribution of the IgG. For example, it may bind the Fc portion of IgG and protect IgG from intracellular catabolism so as to increase its half-life.

A binding molecule such as an antibody or an antigen binding fragment "specifically identifies" or "specifically binds" a target such as human CD3 means it can distinguish the target from one or more reference molecules, and the binding affinity or activity to the target is 1-fold, 5-fold, or 10-fold higher than that to the reference molecules. The method for determining the binding specificity includes, but not limited to, Western Blotting, ELISA, RIA, ECL, IRMA, and peptide scanning.

As used herein, "identity" or "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega, T-coffee, Kalign and MAFFT. When using such software, the default parameters, e.g., for gap penalty and extension penalty, are preferably used.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "CD3" refers to cluster of differentiation 3 which is composed of the γ, δ, ε, and ζ chains. The term "CD3ε" refers to the, chain of the CD3 molecule. The term comprises variants, isoforms, homologs, orthologs and paralogs. For example, an antibody specific for human CD3 (e.g., CD3ε) may, in certain cases, cross-react with CD3 from a species other than human, such as monkey. In other embodiments, an antibody specific for human CD3 (e.g., CD3ε) may be completely specific for human CD3 (e.g., CD3ε) and exhibit no cross-reactivity to CD3 from other species or of other types, or may cross-react with CD3 from certain other species but not all other species. The term "human CD3ε" refers to the CD3ε protein comprising the amino acid sequence from human, such as the CD3ε protein comprising the amino acid sequence with NCBI reference no.: NP_000724.1 (Wipa P et al., (2020) *Immunology* 159 (3): 298-308).

The term "CD20" is a marker molecule expressed on the surface of B cells at various development phases (except stem cells and plasma cells). The term "human CD20" refers to the CD20 comprising the amino acid sequence from human.

The term "cross-linking" or "cross-link" associated with the anti-CD3 antibodies refers to the aggregation of or interaction among the monospecific anti-CD3 antibodies when the Fc regions bind the FcRs on the immune cells, or the aggregation of or interaction among the bispecific antibodies when the non-anti-CD3 binding domains bind the disease associated antigens on target cells. In the in vitro assays, the cross-linking of the anti-CD3 antibodies may occur when the Fc regions bind to secondary antibodies on e.g., ELISA plates. The anti-CD3/CD20 antibodies of the disclosure may only activate T cells when they are cross-linked. The anti-CD3 antibodies in e.g., the scFv format may be cross-linked due to the unstable conformation and inter-cellular interactions.

Engineering or Modifications at Light Chain Framework Region(s)

The antibody molecules with unstable conformations may interact with each other to cause molecule aggregation. Such aggregation may lead to low expression level, poor storage stability, and high immunogenicity, resulting in off-target effects.

The antigen binding fragment without the constant region(s), such as the scFv, is likely to have an unstable conformation. For example, due to the lack of the constant region(s), certain hydrophobic amino acid residues in the VH and the VL may be exposed at the surface, which may destabilize the conformation formed by the VH and the VL. Certain amino acid residues for glycosylation may be exposed at the surface as well, and the glycosylation may destabilize the antibody's conformation and/or decrease the antibody's antigen binding activity. In addition, the lack of the constant region(s) may also lead to unbalanced charge distribution at the surface, which may also bring adverse effect to antibody's conformational stability.

The inventors of the application have found that, certain hydrophobic amino acid residues in the third and fourth framework regions of the light chain variable region, especially the fourth framework region, may be exposed at the surface when the antibody does not contain the constant region(s), which may render the VH-VL interaction unstable. However, the VH-VL interaction may become more stable by replacing these hydrophobic amino acid residue(s) with the amino acid residue(s) that is/are hydrophilic or less hydrophobic. The stabilized VH-VL interaction may decrease the scFv's aggregation propensity and improve its expression level and storage stability. In addition, the inventors of the application further found that the replacement of certain amino acid residues in the third and fourth framework regions, especially the fourth framework region, of the light chain (e.g., the κ light chain) may improve the overall charge distribution to further improve the conformational stability of the antigen binding domain formed by the VH and the VL.

Whether an amino acid residue is hydrophobic or hydrophilic is determined by the groups in its side chains. An amino acid residue is hydrophobic when there are more hydrophobic groups, and vice versa. The hydrophilic groups include the carboxyl group, the sulphonic group, the sulfate group, the phosphate group, the amino group, the quaternary ammonium group, the oxygen-containing group, the ether group, the hydroxyl group, and etc., and the remaining are almost hydrophobic. A hydrophobic amino acid residue is usually located at the interior of a protein and plays an important role in keeping the protein's tertiary structure through its interaction with other hydrophobic groups (see hydrophobic interaction). In addition, the hydrophobic amino acid residues are also involved in the antibody-antigen interaction. For example, the antibody contains a lot of hydrophobic amino acid residues at its antigen binding domain. The hydrophobic amino acid residues include, alanine (Ala), glycine (Gly), valine (Val), leucine (Leu), isoleucine (Ile), phenylalanine (Phe), proline (Pro), methionine (Met), and tryptophan (Trp). The hydrophilic amino acid residues without net charges include threonine (Thr), serine (Ser), aspartate (Asp), glutamine (Gln), and tyrosine (Tyr, Y). The positively charged hydrophilic amino acid residues include lysine (Lys, L), arginine (Arg, R), and histidine (His), while the negatively charged hydrophilic amino acid residues include asparagine (Asn), and glutamate (Glu).

In particular, the disclosure provides a scFv which may comprise a heavy chain variable region, a linker and a light chain variable region. The light chain variable region may comprise a first framework region, a second framework region, a third framework region and a fourth framework region, wherein it is engineered (via e.g., mutation) to comprise leucine (Leu, L) at Position 104, serine (Ser, S) or threonine (Thr, T) (preferably threonine (Thr, T)) at Position 105, alanine (Ala, A), serine (Ser, S) or threonine (Thr, T) (preferably alanine (Ala, A)) at Position 106, according to the Kabat numbering scheme. In addition, the light chain variable region may be engineered (via e.g., mutation) to comprise glutamine (Gln, Q) at Position 100, and/or glutamic acid (Glu, E) at Position 83, according to the Kabat numbering scheme. In one embodiment, the light chain variable region may be engineered (via e.g., mutation) to comprise glutamic acid (Glu, E) at Position 83, according to the Kabat numbering scheme.

The light chain variable region of the disclosure may be also defined by another numbering scheme such as Chothia, IMGT, AbM or Contact, as long as Position 83, 100, and 104 to 106 are the same with those defined by the Kabat numbering scheme.

The light chain framework regions of the scFv of the disclosure may be those from the naturally occurring κ light chain (such as human κ light chain), or those having been engineered on the basis of the naturally occurring κ light chain (such as human κ light chain). The κ light chain may be the scFv scaffold FW1.4gen, 375-FW1.4opt, 435-

FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, 43-FW1.4opt, or the above scaffold with one or more (e.g., 1 to 5) amino acid mutations at the first, second, third and/or fourth framework regions. According to the Kabat numbering scheme, the κ light chain may comprise leucine (Leu, L), threonine (Thr, T) and alanine (Ala, A) at Position 104 to 106, respectively. Further, according to the Kabat numbering scheme, the light chain variable region may comprise glutamine (Gln, Q), leucine (Leu, L), threonine (Thr, T) and alanine (Ala, A) at Position 100, 104 to 106, respectively; may comprise glutamic acid (Glu, E), leucine (Leu, L), threonine (Thr, T) and alanine (Ala, A) at Position 83, 104 to 106, respectively; may comprise glutamic acid (Glu, E) at Position 83; may comprise glutamic acid (Glu, E), glutamine (Gn, Q), leucine (Leu, L), threonine (Thr, T) and alanine (Ala, A) at Position 83, 100, 104 to 106, respectively.

The κ light chain is a member of the immunoglobulin light chain family that is classified by sequence identity and homology. The sequence homology can be determined by homology search matrices such as BLOSUM (Henikoff, S. & Henikoff, J. G., (1992) *Proc. Natl. Acad. Sci. USA* 8910915-10919), and how to classify a light chain based on the sequence homology is well known to those skilled in the art. There are several subfamilies for the κ light chain (see, for instance, Knappik et al., (2000) *J. Mol. Biol.* 29657-29686, where the κ chain is classified as Vκ1 to Vκ4, and the λ light chain is classified as Vλ1 to Vλ3).

In one embodiment, the light chain framework regions are from the κ chain, such as human κ chain, e.g., Vκ1, Vκ2, Vκ3 and Vκ4, especially Vκ1.

According to the Kabat numbering scheme, the light chain framework region(s) of the scFv of the disclosure, after engineered for improved stability, may comprise one or more amino acid residues selected from the group consisting of 83E, 100Q, 104L, 105T, and 106A. In one embodiment, according to the Kabat numbering scheme, the light chain framework region(s) of the disclosure may comprise 83E, 104-106LTA, 83E/104-106LTA, 100Q/104-106LTA, or 83E/100Q/104-106LTA. If the κ chain variable region comprises one or more amino acid residues as required before the engineering, then the engineering or modification (such as amino acid residue mutation(s)) may be applied to the remaining positions, that is, the light chain variable region may be engineered or modified to comprise all the required amino acid residues.

With the engineering, the light chain variable region of the scFv may comprise a fourth framework region of SEQ ID NOs: 33 (X=G) or 35. The light chain variable region of the disclosure may comprise a third framework region of SEQ ID NOs: 32 (X=E) or 34 (X=E), and/or a fourth framework region of SEQ ID NOs: 33 (X=G or Q) or 35. In one embodiment, the light chain variable region may be engineered to comprise a first framework region, a second framework region, a third framework region, and a fourth framework region of SEQ ID NO: 33 (X=G or Q). In one embodiment, the light chain variable region may comprise a first framework region, a second framework region, a third framework region of SEQ ID NO: 32 (X=E), and a fourth framework region of SEQ ID NO: 33 (X=G or Q). In one embodiment, the light chain variable region may comprise a first framework region, a second framework region, a third framework region, and a fourth framework region of SEQ ID NO: 35. In one embodiment, the light chain variable region may comprise a first framework region, a second framework region, a third framework region of SEQ ID NO: 34 (X=E), and a fourth framework region of SEQ ID NO: 35. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the fourth framework region, or the first to fourth framework regions from the light chain variable region of SEQ ID NOs: 16 (X1=V, X2=G, X3=L, X4=T, X5=A; X1=E, X2=G, X3=V, X4=E, X5=I; X1=E, X2=Q, X3=L, X4=T, X5=A) or 24 (X1=E, X2=T, X3=A). The light chain variable region of the disclosure may comprise the third and fourth framework regions, or the first to fourth framework regions from the light chain variable region of SEQ ID NOs: 16 (X1=V, X2=G, X3=L, X4=T, X5=A; X1=E, X2=G, X3=V, X4=E, X5=I; X1=E, X2=Q, X3=L, X4=T, X5=A) or 24 (X1=E, X2=T, X3=A). Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the first, second, third and fourth framework regions comprising the amino acid sequences of SEQ ID NOs: 36, 37, 32 (X=V or E) and 33 (X=G or Q), respectively. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The light chain variable region of the scFv of the disclosure may comprise the first, second, third and fourth framework regions comprising the amino acid sequences of SEQ ID NOs: 38, 39, 34 (X=F or E) and 35, respectively. Optionally, the light chain variable region may comprise one or more (e.g., 1 to 5) amino acid mutations at the first, the second and the third framework regions. Optionally, the light chain variable region may comprise one or more (e.g., 1 to 5) amino acid mutations at the first and the second framework regions.

The amino acid mutation(s), other than those at the positions key to the light chain variable region's stability, is/are herein preferably conservative, which does/do not significantly affect or alter the binding characteristics, especially the binding affinity/activity, of the antibody or the antigen binding fragment. Such conservative modifications include amino acid substitutions, additions and deletions. Modifications can be introduced into the light chain framework region(s) of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the framework region(s) of the disclosure can be replaced with other amino acid residues from the same side chain family and the altered antibody or antigen binding fragment can be tested for retained function (e.g., the antigen binding capability, antibody stability, and aggregation propensity) using the functional assays described herein.

The framework region(s) in the light chain variable region of the scFv of the disclosure may be further engineered to improve the scFv's stability. For example, an appropriate linker may be used. The length of the linker between the VH and the VL may affect the scFv's stability. The VH and the VL cannot interact well with a linker that is much too short, and a scFv with a much too long linker may adversely affect the scFv's expression and rigidity. The sulfide bond(s) may be introduced to the interface where the VH and the VL meet, which may keep the scFv in a closed status, so as to inhibit scFv aggregation.

Preparation of Antibodies or Antigen Binding Fragments with Engineered Light Chain Framework Region(s)

The disclosure also provides a method for preparing an antibody or an antigen binding fragment, comprising introducing the nucleotides encoding the VL-CDR1, VL-CDR2 and VL-CDR3 into the nucleotides encoding the framework regions of the disclosure.

When an antibody or an antigen binding fragment is to be humanized, the engineering or modification of the light chain variable region may be performed along with the CDR grafting. In specific, appropriate framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase). As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo 12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678). Antibody protein sequences are compared against a compiled protein sequence database using one of the sequence similarity searching methods called the Gapped BLAST, which is well known to those skilled in the art. Preferred framework sequences for use in the antibodies of the disclosure are those that are structurally similar to the framework sequences used by antibodies of the disclosure. The VH CDR1, CDR2, and CDR3 sequences can be grafted onto framework regions that have the identical sequence as that found in the germline immunoglobulin gene from which the framework sequence derives, or the CDR sequences can be grafted onto framework regions that comprise one or more mutations as compared to the germline sequences. For example, it has been found that in certain instances it is beneficial to mutate residues within the framework regions to maintain or enhance the antigen binding ability of the antibody. The CDR grafting in the light chain may comprise, with the methods known to the skilled in the art, i) replacing the nucleotides in a nucleic acid construct such as a recombinant vector encoding the amino acid residues at Position 104, 105 and 106 with those encoding leucine (Leu, L), serine (Ser, S)/threonine (Thr, T), and alanine (Ala, A)/serine (Ser, S)/threonine (Thr, T), respectively, optionally replacing the nucleotides encoding the amino acid residue at Position 100 with those encoding glutamine (Gln, Q), and optionally replacing the nucleotides encoding the amino acid residue at Position 83 with those encoding glutamic acid (Glu, E); ii) introducing the nucleotides coding for the VL-CDR1, VL-CDR2 and VL-CDR3 to the nucleic acid construct, and iii) expressing the antibody or antigen binding fragment in the nucleic acid construct under a suitable condition. Alternatively, the CDR grafting in the light chain may comprise: i) replacing the nucleotides encoding the fourth framework region with those encoding SEQ ID NO: 33 (X=G or Q), optionally replacing the nucleotides encoding the third framework region with those encoding SEQ ID NO: 32 (X=E), and optionally replacing the nucleotides encoding the first and second framework regions with those encoding SEQ ID NOs: 36 and 37, respectively; or alternatively, replacing the nucleotides encoding the fourth framework region with those encoding SEQ ID NO: 35, optionally replacing the nucleotides encoding the third framework region with those encoding SEQ ID NO: 34 (X=E), and optionally replacing the nucleotides encoding the first and second framework regions with those encoding SEQ ID NOs: 38 and 39, respectively, in the nucleic acid construct (e.g., a recombinant vector) comprising the nucleic acid coding the light chain, ii) introducing the nucleotides coding for the VL-CDR1, VL-CDR2 and VL-CDR3 to the nucleic acid construct, and iii) expressing the antibody or antigen binding fragment in the nucleic acid construct under a suitable condition.

If a scFv is constructed with a naturally occurring antibody without CDR grafting, work can be focused on the engineering of or modification on the framework regions in the light chain variable region. In other words, only the replacement of the nucleotides encoding the key amino acid residues in the third framework region, or the third and fourth framework regions is required.

During the recombinant construction, according to the Kabat numbering scheme, if the original light chain variable region comprises one or more amino acid residues as required at the key positions, then the engineering or modification may be applied to the remaining positions.

Bispecific Antibodies

The disclosure provides a bispecific antibody targeting CD3 and CD20, with all or part of the antibody binding domains contain the light chain framework regions of the disclosure.

The bispecific antibody may comprise one anti-CD3 Fv or Fab, one anti-CD20 Fv or Fab, and one anti-CD20 scFv. The anti-CD20 scFv may comprise the engineered light chain framework region(s) of the disclosure.

The anti-CD20/CD3 bispecific antibody may be an IgG like antibody. The IgG like antibody may be one generated by making a few modifications on the basis of an IgG antibody, such as an antibody obtained by linking a peptide chain, e.g., a scFv, to the N-terminus or the C-terminus of the heavy chain and/or the light chain of an IgG antibody. In one embodiment, the bispecific antibody may comprise an anti-CD3 IgG half antibody, an anti-CD20 IgG half antibody, and an anti-CD20 scFv linked to the N-terminus or the C-terminus of the heavy chain variable region or the light chain variable region of the anti-CD3 IgG half antibody.

In an embodiment, the bispecific antibody may comprise:

i) a first polypeptide chain, comprising an anti-CD20 heavy chain variable region, and a heavy chain constant region;

ii) a second polypeptide chain, comprising an anti-CD20 light chain variable region;

iii) a third polypeptide chain, comprising an anti-CD20 heavy chain variable region, an anti-CD20 light chain variable region, an anti-CD3ε heavy chain variable region, and a heavy chain constant region; and iv) a fourth polypeptide chain, comprising an anti-CD3ε light chain variable region, wherein the anti-CD20 heavy chain variable region in the first polypeptide chain may associate with the anti-CD20 light chain variable region in the second polypeptide chain to form an anti-CD20 antigen binding fragment, the anti-CD20 heavy chain variable region and the anti-CD20 light chain variable region in the third polypeptide chain may associate to form an anti-CD20 antigen binding fragment, the anti-CD3ε heavy chain variable region in the third polypeptide chain may associated with the anti-CD3ε light chain variable region in the fourth polypeptide chain to form an anti-CD3 antigen binding fragment, and the heavy chain constant region in the first polypeptide chain and the constant region in the third polypeptide chain are bonded covalently, or via e.g., the knobs-into-holes approach, or the disulfide bond(s).

In another embodiment, the bispecific antibody may comprise:

i) a first polypeptide chain, comprising an anti-CD20 heavy chain variable region, and a heavy chain constant region;

ii) a second polypeptide chain, comprising an anti-CD20 light chain variable region;

iii) a third polypeptide chain, comprising an anti-CD3ε heavy chain variable region and a heavy chain constant region; and iv) a fourth polypeptide chain, comprising an anti-CD20 heavy chain variable region, an anti-CD20 light chain variable region, and an anti-CD3ε light chain variable region, wherein the anti-CD20 heavy chain variable region in the first polypeptide chain may associate with the anti-CD20 light chain variable region in the second polypeptide chain to form an anti-CD20 antigen binding fragment, the anti-CD3ε heavy chain variable region in the third polypeptide chain and the anti-CD3ε light chain variable region in the fourth polypeptide chain may associate to form an anti-CD3 antigen binding fragment, the anti-CD20 heavy chain variable region and the anti-CD20 light chain variable region in the fourth polypeptide chain may associate to form an anti-CD20 antigen binding fragment, and the heavy chain constant region in the first polypeptide chain and the heavy chain constant region in the third polypeptide chain are bonded covalently, or via e.g., the knobs-into-holes approach, or the disulfide bond(s).

In the bispecific antibody, the anti-CD20 heavy chain variable region may be linked, via a linker, to the anti-CD20 light chain variable region. The anti-CD20 heavy chain variable region or the anti-CD20 light chain variable region may be linked via a linker to the anti-CD3 antibody or antigen binding fragment.

The linker may be made up of amino acids linked together by peptide bonds, preferably from 15 to 30 amino acids linked by peptide bonds, wherein the amino acids are selected from the 20 naturally occurring amino acids. One or more of these amino acids may be glycosylated, as is understood by those of skill in the art. In one embodiment, the 15 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, poly(Gly-Ala), and polyalanines. The exemplary linker is set forth in SEQ ID NOs: 27, 28 or 29.

Linkers may also be non-peptide linkers. For example, alkyl linkers such as —NH—, —$(CH_2)$s-C(O)—, wherein s=2-20 can be used. These alkyl linkers may further be substituted by any non-sterically hindering group such as lower alkyl (e.g., $C_{1-6}$) lower acyl, halogen (e.g., Cl, Br), CN, $NH_2$, phenyl, etc.

The bispecific antibody of the disclosure may comprise a heavy chain variable region and/or a light chain variable region or CDR1, CDR2 and CDR3 with one or more conservative modifications. It is known in the art that some conservative modifications may not affect the antigen binding affinity. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

The term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into the bispecific antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain.

Engineered Bispecific Molecules

The bispecific molecules of the disclosure can be prepared using a bispecific molecule having one or more of the $V_H$/$V_L$ sequences of the present disclosure as the starting material. The bispecific antibody can be engineered by modifying one or more residues within one or both variable regions (i.e., $V_H$ and/or $V_L$), for example within one or more CDR regions and/or within one or more framework regions, to improve the binding affinity and/or to increase similarity to some naturally occurring antibodies. Additionally or alternatively, an antibody can be engineered by modifying residues within the constant region(s), for example to alter the effector function(s) of the antibody.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back-mutate" one or more framework residues to the corresponding germline sequence. More specifically, an antibody that has undergone somatic mutation can comprise framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody.

In addition, or as an alternative to modifications made within the framework or CDR regions, the bispecific molecules of the disclosure can be engineered to include modifications within the Fe region, typically to alter one or more functional properties, such as serum half-life, complement fixation, Fc receptor binding, and/or antigen-dependent cellular cytotoxicity. Furthermore, a bispecific molecule of the disclosure can be chemically modified (e.g., one or more chemical moieties can be attached to the molecule) or be modified to alter its glycosylation, again to alter one or more functional properties of the bispecific molecule.

In one embodiment, the hinge region at the $C_{H1}$ region is modified such that the number of cysteine residues in the hinge region is altered, e.g., increased or decreased. The number of cysteine residues in the hinge region is altered to, for example, facilitate assembly of the light and heavy chains or to increase or decrease the stability of the antibody.

In another embodiment, the Fc hinge region of the bispecific molecule is mutated to increase or decrease the biological half-life. More specifically, one or more amino acid mutations are introduced into the $C_{H2}$-$C_{H3}$ domain interface region of the Fc-hinge fragment such that the bispecific molecule has impaired Staphylococcyl protein A (SpA) binding relative to native Fc-hinge domain SpA binding.

In still another embodiment, the glycosylation of a bispecific molecule is modified. For example, a de-glycosylated bispecific molecule can be made (i.e., the bispecific molecule lacks glycosylation). Glycosylation can be altered to, for example, increase the affinity of the bispecific molecule for the antigen(s). Such carbohydrate modifications can be accomplished by, for example, altering one or more sites of glycosylation within the molecule sequence. For example, one or more amino acid substitutions can be made that result in elimination of one or more variable region framework glycosylation sites to thereby eliminate glycosylation at that site. Such a glycosylation may increase the affinity of the molecule for the antigen(s).

Another modification of the bispecific molecules herein that is contemplated by this disclosure is pegylation. A bispecific molecule can be pegylated to, for example, increase the biological (e.g., serum) half-life of the molecule. To pegylate a bispecific molecule, the molecule typically is reacted with polyethylene glycol (PEG), such as a reactive ester or aldehyde derivative of PEG, under conditions in which one or more PEG groups become attached to the molecule. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Nucleic Acid Molecules Encoding Antibodies or Antigen Binding Fragments

The disclosure provides a nucleic acid molecule encoding the antibody or antigen binding fragment such as a scFv as well as the bispecific molecule or the functional fragment thereof of the disclosure.

The nucleic acid molecule can be present in whole cells, in a cell lysate, or in a partially purified or substantially pure form. A nucleic acid molecule is "isolated" or "rendered substantially pure" when purified away from other cellular components or other contaminants, e.g., other cellular nucleic acids or proteins, by standard techniques. A nucleic acid molecule of the disclosure can be, e.g., DNA or RNA and may or may not contain intronic sequences. In a preferred embodiment, the nucleic acid molecule is a cDNA molecule.

The nucleic acid molecule of the disclosure can be obtained using standard molecular biology techniques. For instance, the DNA fragment(s) encoding the CDR(s) may be operatively linked to the DNA fragment(s) coding for the framework region(s) (e.g., the light chain framework region(s) of the disclosure); the DNA fragment(s) encoding the VH and VL may be operatively linked to those encoding the heavy chain constant region and the light chain constant region. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$ (SEQ ID NO: 27), such that the $V_H$ and $V_L$ sequences can be expressed as a contiguous single-chain protein, with the $V_L$ and $V_H$ regions joined by the flexible linker (see e.g., Bird et al., (1988) *Science* 242:423-426;

Huston et al., (1988) *Proc. Natl. Acad. Sci. USA* 85:5879-5883; McCafferty et al., (1990) *Nature* 348:552-554).

The nucleotides encoding the polypeptide chains of the disclosure may be inserted into one or more expression vectors where the polypeptide chain-coding nucleotides are operatively linked to the regulatory sequences. The expression vectors may be transfected into host cells for expression of the polypeptide chains.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which comprises sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The recombinant expression vector can encode a signal peptide that facilitates secretion of the polypeptide chains from a host cell. The polypeptide chain gene can be cloned into the vector such that the signal peptide is linked in-frame to the amino terminus of the polypeptide chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

The expression vector(s) may be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the polypeptide chains of the disclosure in either prokaryotic or eukaryotic host cells, expression in eukaryotic cells, and most preferably mammalian host cells, is the most preferred because such eukaryotic cells, and in particular mammalian cells, are more likely than prokaryotic cells to assemble and secrete a properly folded and immunologically active antibody.

Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

Preferred mammalian host cells for expressing the recombinant bispecific antibodies of the disclosure include Chinese Hamster Ovary (CHO cells) (including dhfr− CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841.

Pharmaceutical Compositions

In another aspect, the present disclosure provides a pharmaceutical composition which may comprise the antibody (including the bispecific antibody) or antigen binding fragment with the engineered light chain framework region(s), the nucleic acid molecule encoding the antibody or antigen binding fragment, the expression vector containing the nucleic acid molecule, and/or the host cell containing the expression vector or having the nucleic acid molecule incorporated into its genome, of the disclosure, formulated together with a pharmaceutically acceptable carrier. The composition may optionally comprise one or more additional pharmaceutically active ingredients, such as an anti-tumor agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof.

The pharmaceutical composition may be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition of the disclosure can be administered via a non-parenteral route, such as a topical, epidermal or mucosal route of administration, e.g., intranasally, orally, vaginally, rectally, sublingually or topically.

The pharmaceutical compositions can be in the form of sterile aqueous solutions or dispersions. They can also be formulated in a microemulsion, liposome, or other ordered structure suitable to high drug concentration.

The amount of the active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit comprises a predetermined quantity of active ingredient calculated to produce the desired therapeutic effect in association with the required pharmaceutical carrier. Alternatively, the antibody or antigen binding fragment of the disclosure can be administered as a sustained release formulation, in which case less frequent administration is required.

The administration of the pharmaceutical composition may be determined by the medical care personnel depending on the gender, age, medical history and the like of the subject.

A "therapeutically effective dosage" of the antibody or antigen binding fragment of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the antibodies of the disclosure can be formulated to ensure proper distribution in vivo. For example, to ensure that the therapeutic antibody of the disclosure can cross the blood-brain barrier, they can be formulated in liposomes, which may additionally comprise targeting moieties to enhance selective transport to specific cells or organs.

Methods and Uses

The framework regions in the light chain variable region may be engineered during the generation of an antibody or an antigen binding fragment, e.g., a scFv, with no constant region(s), to improve the antibody or antigen binding fragment's stability, aggregation propensity and expression level, and to reduce the off-target effect and the immunogenicity.

The antibody or antigen binding fragment, such as the anti-CD3/CD20 bispecific antibody, with the light chain framework region engineered according to the disclosure, has reduced aggregation propensity. Such an anti-CD3/CD20 bispecific antibody may decrease T cell-mediated non-specific immunity so as to relieve the side effects which is beneficial to the tumor treatment.

The anti-CD3/CD20 bispecific antibody of the disclosure may be used to treat or relieve B cell associated diseases. In certain embodiments, the B cell associated disease may be B-cell lymphoma, B-cell leukemia, or a B cell-mediated autoimmune disease. In certain embodiments, B-cell lymphoma and B-cell leukemia include, but not limited to, non-Hodgkin's lymphoma (NHL), chronic lymphocytic leukemia (CLL), and diffuse large B-cell lymphoma (DLBCL). In one embodiment, the subject may be administered with an anti-CD20 antibody before the administration of the bispecific molecule of the disclosure.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present application is now further described with the non-limiting examples below.

EXAMPLES

Example 1. Design of scFv Mutants with Enhanced Stability

Usually, the Fab fragment is much more stable in conformation than the corresponding scFv.

In pymol (a molecular visualization system), the Fab crystal conformation (PDB ID.: 6NOV, FIG. 1A) and the scFv crystal conformation (PDB ID.: 6NOU, FIG. 1B) of ixekizumab, an antibody that is known in the art, were superimposed (FIG. 1C). It can be seen that the conformations of the heavy chain variable region (VH) and the light chain variable region (VL) were almost the same in the scFv and the Fab formats. However, some hydrophobic amino acid residues were exposed at the C-terminus of the VL in the scFv (FIG. 1B) which may render the whole conformation less stable, while these hydrophobic amino acid residues were covered by the light chain constant region (CL) in the Fab format (FIG. 1A).

The exposure of hydrophobic residues at the C-terminus of the VL may cause scFv aggression, which may further lead to high immunogenicity, low production level, off-target effect, and etc. To solve these problems, the inventors of the application tried to modify the VL at the C-terminus.

In particular, the inventors analyzed the C-terminus of the light chain variable region (κ chain) of the scFv. It usually contained a hydrophobic amino acid residue, e.g., phenylalanine (Phe, F), valine (Val, V) or isoleucine (Ile, I), at Position 83 (according to the Kabat numbering scheme), and a hydrophobic amino acid residue, e.g., isoleucine (Ile, I), at Position 106, which were both exposed at the surface. The residues at these two positions commonly interact with the hydrophobic amino acid residue at Position 104, e.g., leucine (Leu, L) or valine (Val, V) which was located at the interior of the light chain variable region. To reduce the hydrophobicity at the C-terminus of the light chain variable region, the amino acid residue at Position 83 was replaced with the hydrophilic serine (Ser, S), threonine (Thr, T), aspartic acid (Asp, D), or glutamic acid (Glu, E), preferable glutamic acid (Glu, E); and the amino acid residue at Position 106 was replaced with the less hydrophobic alanine (Ala, A), serine (Ser, S) or threonine (Thr, T), preferably alanine (Ala, A). Glutamic acid (Glu, E), the negatively charged amino acid residue at Position 105 was replaced with serine (Ser, S) or threonine (Thr, T) with no net charge, for the overall charge balance. Several light chain framework regions were designed, the details of which can be found in Table 1 below.

TABLE 1

Wildtype and mutated framework region(s) in kappa light chain variable region

| | Third framework region | Fourth framework region |
|---|---|---|
| Wildtype | No mutation | No mutation |
| Mutant 1 | No mutation | 104-106LTA |
| Mutant 2 | 83E | No mutation |
| Mutant 3 | 83E | 104-106LTA |
| Mutant 4 | 83E | 100Q, 104-106LTA |

Example 2. Generation of Bispecific Antibodies with Wildtype or Mutated scFv

Figure 2:
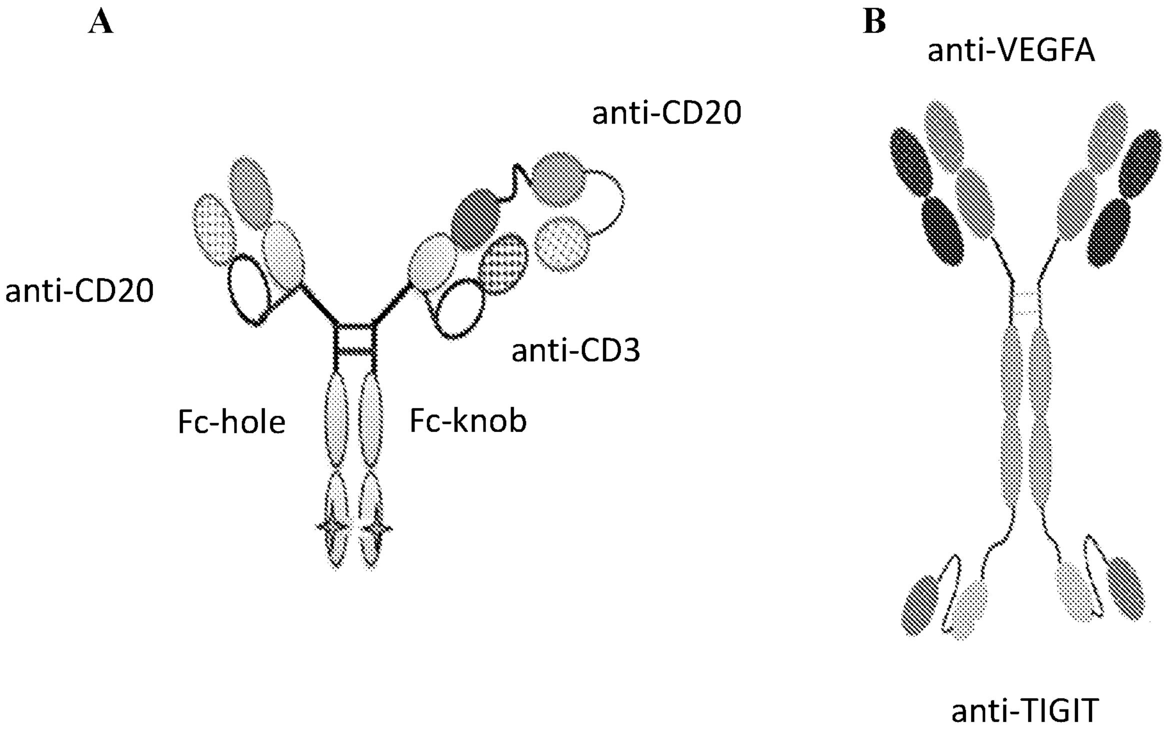
FIG. 2 is a schematic diagram of structures of an anti-CD3/CD20 bispecific antibody (A) and an anti-TIGIT/VEGF bispecific antibody (B).

An anti-CD3/CD20 antibody and an anti-TIGIT/VEGF antibody were constructed using the light chain framework region(s) as designed in Example 1 and tested for their conformational stability. The structures of these two bispecific antibodies were shown in FIG. 2.

In particular, the anti-CD3/CD20 bispecific antibody was asymmetric in structure, comprising an anti-CD20 half antibody, and an anti-CD3 half antibody, with an anti-CD20 scFv linked to the N-terminus of the heavy chain of the anti-CD3 half antibody. The bispecific antibody was referred to as MBS303 when containing the wildtype light chain framework region(s), and referred to as MBS303m when containing the framework mutant of Example 1. Using the GS expression vectors, the anti-CD20 half antibody MIL220 (for construction of MBS303 and MBS303m, comprising the anti-CD20 heavy chain of SEQ ID NO: 21 with a hole heavy chain constant region, and the anti-CD20 light chain of SEQ ID NO: 23), the anti-CD3 half antibody with anti-CD20 scFv MIL221-2 (for construction of MBS303, comprising the anti-CD20 VH-linker-anti-CD20 VL-linker-anti-CD3 VH-heavy chain constant region (with a knob) chain of SEQ ID NO: 30, and the anti-CD3 light chain of SEQ ID NO: 22), and the anti-CD3 half antibody with anti-CD20 scFv MIL221-3 (for construction of MBS303m, comprising the anti-CD20 VH-linker-anti-CD20 VL (with V104L/E105T/I106A, V83E, or V83E/G100Q/V104L/E105T/I106A)-linker-anti-CD3 VH-heavy chain constant region (with a knob) chain of SEQ ID NO: 20 (X1=V, X2=G, X3=L, X4=T, X5=A; X1=E, X2=G, X3=V, X4=E, X5=I; X1=E, X2=Q, X3=L, X4=T, X5=A), and the anti-CD3 light chain of SEQ ID NO: 22) were generated.

The anti-TIGIT/VEGF bispecific antibody was symmetric in structure, comprising an anti-VEGF antibody, and two anti-TIGIT scFvs linked to the two anti-VEGF heavy chains at the C-terminus. The bispecific antibody was referred to as MBS310 when the scFv contained the wildtype light chain framework region(s), and referred to as MBS310m when the scFv contained the framework mutant of Example 1. In specific, MBS310 contained four polypeptide chains of SEQ ID NOs: 25 (X1=F, X2=E, X3=L), 26, 25 (X1=F, X2=E, X3=L) and 26, respectively, and MBS310m contained four polypeptide chains of SEQ ID NOs: 25 (X1=E, X2=T, X3=A), 26, 25 (X1=E, X2=T, X3=A), and 26, respectively, wherein the light chain variable region in the scFv of MBS310m contained the F83E/L104L/E105T/L106A mutations.

The DNA fragments encoding the long (heavy) chains (comprising the variable region and the constant region) and the short (light) chains (comprising the variable region and the constant region) of the MIL220, MIL221-2, MIL221-3, MBS310 and MBS310m were synthesized. The short (light) chain-coding nucleotides were digested with ClaI and HindIII, and those coding for the long (heavy) chains were treated with EcoRI and XhoI. The pCMV plasmids were digested by HindIII and EcoRI, while the GS-vectors were digested by ClaI and XhoI. The DNA fragments were recovered, purified, ligated, and transformed into bacteria. Single bacterial colonies were picked up and sequenced, and expression vectors containing the correct sequences were obtained. The MBS310 and MBS310m were expressed with the single-cell system, while the MBS303 and MBS303m were expressed in the dual-cell system and assembled in vitro.

HEK-293F cells (Cobioer, China) were transfected with the expression vectors obtained above using PEI. Briefly, HEK-293F cells were transfected with the expression vectors using polyethyleneinimine (PEI) at a DNA:PEI ratio of 1:3. The concentration of DNAs used for transfection was 1.5 μg/ml. The transfected HEK-293F cells were cultured in an incubator in 5% $CO_2$ at 37° C. with shaking at 120 RPM. After 10-12 days, cell culture supernatants were harvested, and subject to centrifugation at 3500 rpm for 5 minutes and then to filtration using 0.22 μm films to remove cell debris. The molecules as expressed were then purified and enriched using a pre-equilibrated Protein-A affinity column (Cat #:17040501, GE, USA) and eluted with the elution buffer (20 mM citric acid, pH3.0-3.5). The purified molecules were kept in PBS buffer (pH 7.0) and the concentration was determined using a NanoDrop™ spectrophotometer instrument.

The expression levels of the antibodies, including the half antibodies, were determined by NanoDrop™, and summarized in Table 2 below.

The MBS303 and MBS303m were assembled in vitro. Briefly, the purified half antibodies, i.e., MIL220 and MIL221-2, or alternatively MIL220 and MIL221-3, were mixed at a 1:1 molar ratio. The mixtures were added with Tris base buffer till pH 8.0 followed by reduced glutathione, and allowed to react overnight at 25° C. with low-speed stirring. Then, the mixtures were added with 2 M acetic acid solution to adjust pH to 5.5. The reducing agent was removed by ultrafiltration, to terminate the reaction. The antibodies as assembled were purified using anion exchange chromatography and cation exchange chromatography. Anion exchange columns were balanced with low-salt Tris buffer (pH8.0), and loaded with the antibody samples. The components that had passed through the columns were collected, and rinsed by low-salt Tris buffer (pH8.0) until UV280 trended to the baseline. The collected samples were adjusted to pH5.5 using an acetic acid solution, concentrated to 1 ml using a 30 kDa ultrafilter tube, and filtered using 0.2 μm membrane. Cation exchange columns were balanced with a low-concentration acetate buffer (pH5.5), and loaded with the antibody samples. The low-concentration acetate buffer (pH5.5) was used to balance the columns again, and elution was done using 20 CV acetate solutions (concentration at 0-100%, pH5.5).

As shown in Table 2, after the framework region(s) of the light chain variable region in the anti-CD20 or anti-TIGIT scFv was/were modified, the expression levels of the antibodies, including the half antibodies, increased significantly. In specific, the expression level of the MIL221-3 with the key LTA mutations was 1.9-fold (with 104-16LTA) or 2.9-fold (with 83E, 100Q and 104-106LTA) higher than that with the wildtype framework region(s), while the expression level of-MBS31m with the key LTA mutations (83E and 104-106LTA) was 1.9-fold higher than that of MBS310. The results indicated that the scFv with the engineered light chain framework regions rendered the bispecific antibodies more stable, resulting in higher recombinant expression levels.

TABLE 2

Expression levels of symmetric antibodies and asymmetric half antibodies

| Antibody ID | Expression amount in supernatants (mg/L) | Expression level change vs. wildtype framework regions(s) |
|---|---|---|
| MIL220 | 73.28 | — |
| MIL221-2 (with wildtype framework regions) | 17.7 | — |
| MIL221-3 (with 104-106LTA) | 51.95 | 1.9-fold increase |
| MIL221-3 (with 83E) | 33.74 | 0.9-fold increase |
| MIL221-3 (with 83E, 100Q, 104-106LTA) | 68.26 | 2.9-fold increase |
| MBS310 (with wildtype framework regions) | 9.9 | — |
| MBS310m (with 83E, 104-106LTA) | 28.91 | 1.9-fold increase |

Example 3. Homogeneity of Bispecific Antibodies with Wildtype or Mutated scFv The MBS303, MBS303m, MBS310 and MBS310m were purified and subjected to the size exclusion-high-performance liquid chromatography (SEC-HPLC). Briefly, the antibody samples were concentrated to 2 mg/ml, and had the components separated using the size exclusion chromatography columns (G3000SW). The amounts of the monomers, aggregates and fragments were calculated according to the peak areas. The results were shown in Table 3 below.

As shown in Table 3, with the engineering or modification at the framework region(s) of the light chain variable region of the scFv, the bispecific antibodies with the key LTA mutations were present with increased monomers, as compared to the unmodified ones. In particular, the monomers of MBS303m (with 83E, 100Q, and 104-106LTA) and MBS310m (with 83E, and 104-106LTA) increased by 14.7% and 16.9%, respectively.

TABLE 3

Aggregation propensity of bispecific antibodies

| Antibody ID | Aggregate (%) | Monomer (main peak, %) | Fragment (%) |
|---|---|---|---|
| MBS303 (with wildtype framework regions) | 14.2 | 77.6 | 8.2 |
| MBS303m (with 104-106LTA) | 1.4 | 78.3 | 20.2 |
| MBS303m (with 83E) | 5.3 | 80.9 | 13.8 |
| MBS303m (with 83E, 100Q, 104-106LTA) | 7.7 | 92.3 | 0 |
| MBS310 (with wildtype framework regions) | 23.5 | 76.5 | 0 |
| MBS310m (with 83E, 104-106LTA) | 6.5 | 93.4 | 0.1 |

Example 4. Thermal Stability of Bispecific Antibodies with Wildtype or Mutated scFv The purified MBS303 and MBS303m were stored at 42° C. (high temperature) for two weeks and subjected to size exclusion-high-performance liquid chromatography to check any change in aggregation propensity and etc. Briefly, the samples were concentrated to 2 mg/ml and had the components separated using the size exclusion chromatography columns (G3000SW). The amounts of the monomers, aggregates and fragments were calculated according to the peak areas. The results were shown in Table 4 below.

TABLE 4

Aggregation propensity of bispecific antibodies

| Antibody ID | Aggregate (%) | Monomer (main peak, %) | Fragment (%) |
|---|---|---|---|
| MBS303 (with wildtype framework regions)- stored under normal storage condition | 3.4 | 95.7 | 0.9 |
| MBS303 (with wildtype framework regions)- after 2-week high temperature storage | 9.5 | 88.8 | 1.6 |
| MBS303m (with 83E, 100Q, 104-106LTA)- stored under normal storage condition | 0.9 | 96.0 | 3.1 |
| MBS303m (with 83E, 100Q, 104-106LTA) - after 2-week high temperature storage | 2.5 | 96.5 | 1.1 |

According to Table 4, the bispecific antibodies with the engineered scFv had better thermal stability. In other words, nearly no decrease in the monomer amount was observed after the high temperature storage. For the bispecific antibodies without scFv engineering, significantly more aggregates were found after high temperature storage.

Example 5. Binding Activity of Bispecific Antibodies with Wildtype or Mutated scFv To assess the influence of the scFv engineering on the biological activity of the bispecific antibodies, MBS303 and MBS303m were tested for their binding activity to Raji cells ($CD20^+$ tumor cells) and Jurkat cells ($CD3^+$ tumor cells), and MBS301 and MBS310m were tested using the HEK293A/TIGIT cells (HEK293A cells over-expressing human TIGIT), by fluorescence-activated cell sorting. In addition, MBS310 and MBS310m were further tested in ELISA for human VEGF binding activity.

Firstly, the HEK293A/TIGIT cells were constructed as follows. Briefly, the cDNA sequence encoding human TIGIT (the amino acid sequence set forth in SEQ ID NO: 31) was synthesized, and then subcloned into the pLV-EGFP (2A)-Puro vector (Beijing Inovogen, China). Lentiviruses were generated in HEK293T cells (Cobioer, NJ, China) by cotransfection of the resultant pLV-EGFP(2A)-Puro-TIGIT, psPAX and pMD2.G plasmids, according to the instruction in the cationic-lipid transfection reagents kit, the Lipofectamine™ 3000 kit (Thermo Fisher Scientific, USA). Three days post cotransfection, the lentiviruses were harvested from the HEK293T cell culture (DMEM medium (Cat #: SH30022.01, Gibco) added with 10% FBS (Cat #: FND500, Excell)), and then used to infect HEK293A cells (Cobioer, China) to generate HEK293A cell lines stably expressing human TIGIT, namely HEK293A/TIGIT cells. The transfected HEK293A cells were cultured in DMEM containing 10% FBS and 0.2 g/ml puromycin (Cat #: A11138-03, Gibco) for 7 days. The expression of human TIGIT was confirmed by fluorescence-activated cell sorting using the commercially available anti-human TIGIT antibody (PE anti-human TIGIT Antibody, Cat #: 372703, Biolegend, China) by fluorescence-activated cell sorting in a flow cytometer.

For the assay to test the MBS303 and MBS303m' binding activity to Raji and Jurkat cells, 105 Raji or Jurkat cells were plated on 96-well ELISA plates in 100 µl cell culture medium, and the ELISA plates were added with 50 µl serially diluted MBS303 and MBS303m, respectively. After incubation at 4° C. for 1 h, the ELISA plates were washed with PBST for three times, and added with APC-goat anti-mouse IgG (1:500, Cat #: 405308, BioLegend, US). The ELISA plates were incubated 4° C. for 1 h, washed with PBS for three times, and subject to the BD flow cytometry system for fluorescence-activated cell sorting.

The MBS310 and MBS310m were tested for their binding activity to the HEK293A/TIGIT cells prepared above, by fluorescence-activated cell sorting, following the protocol above, except HEK293A/TIGIT cells were used instead of the Raji or Jurkat cells.

For the assay for testing the VEGF binding activity, the ELISA plates were coated with 100 µl 500 ng/ml human VEGF-A (Cat #: 11066-HNAN, Sino Biological, China) overnight at 4° C. Then, each well in the ELISA plates was blocked with 200 µl blocking buffer (PBS+1% BSA+1% goat serum+0.05% Tween 20) at room temperature for 2 h, and then added and incubated with 100 µl serially diluted MBS310 or MBS310m (concentration starting at 40 g/ml) at room temperature for 1 h. The ELISA plates were washed by PBST (PBS+0.05% Tween 20) for three times, and added and incubated with HRP conjugated goat anti-mouse IgG (1:5000, Cat #: A9309-1 ml, Sigma, USA) at room temperature for 1 h. The ELISA plates were added with freshly prepared Ultra-TMB (Cat #: 555214, BD, USA) for 5-min color development, and the absorbance of each well was read on a microplate reader (SpectraMax® i3X, Molecular Devices, USA) at 450 nm.

Figure 3:
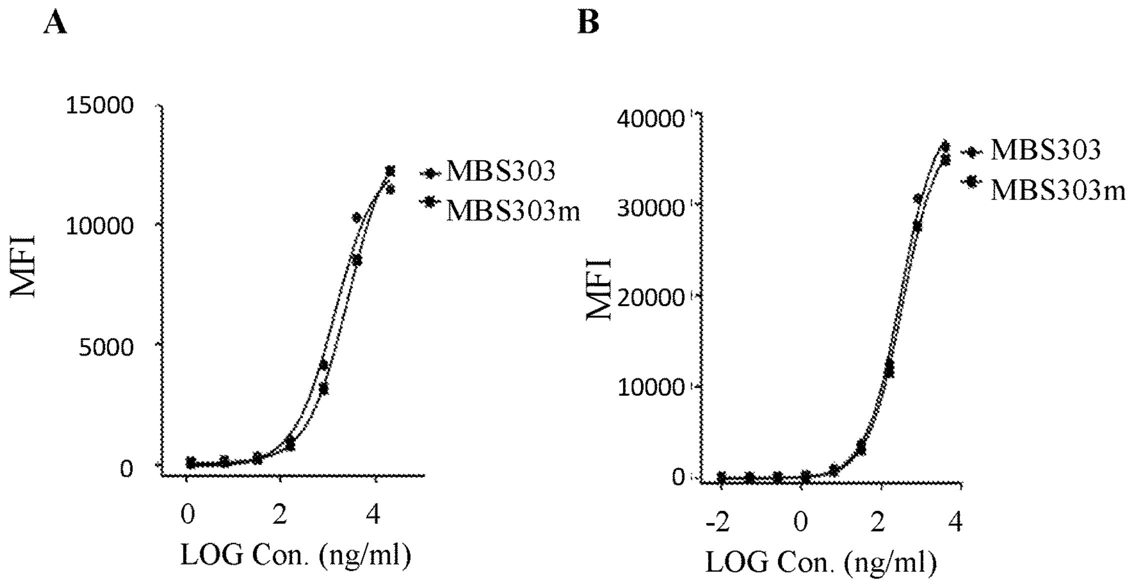
FIG. 3 shows the binding activity of two anti-CD3/CD20 bispecific antibodies MBS303 and MBS303m to $CD3^+$ Jurkat cells (A) and $CD20^+$ Raji cells (B).

The binding activity of MBS303 and MBS303m to Raji and Jurkat cells was shown in FIG. 3. It can be seen that MBS303 and MBS303m (with 83E, 100Q and 104-106LTA) showed comparable binding activity to the $CD20^+$ Raji cells and the $CD3^+$ Jurkat cells, suggesting that the engineering or modification at the light chain framework region(s) of the scFv had little or no influence on the bispecific antibodies' target binding capability.

Figure 4:
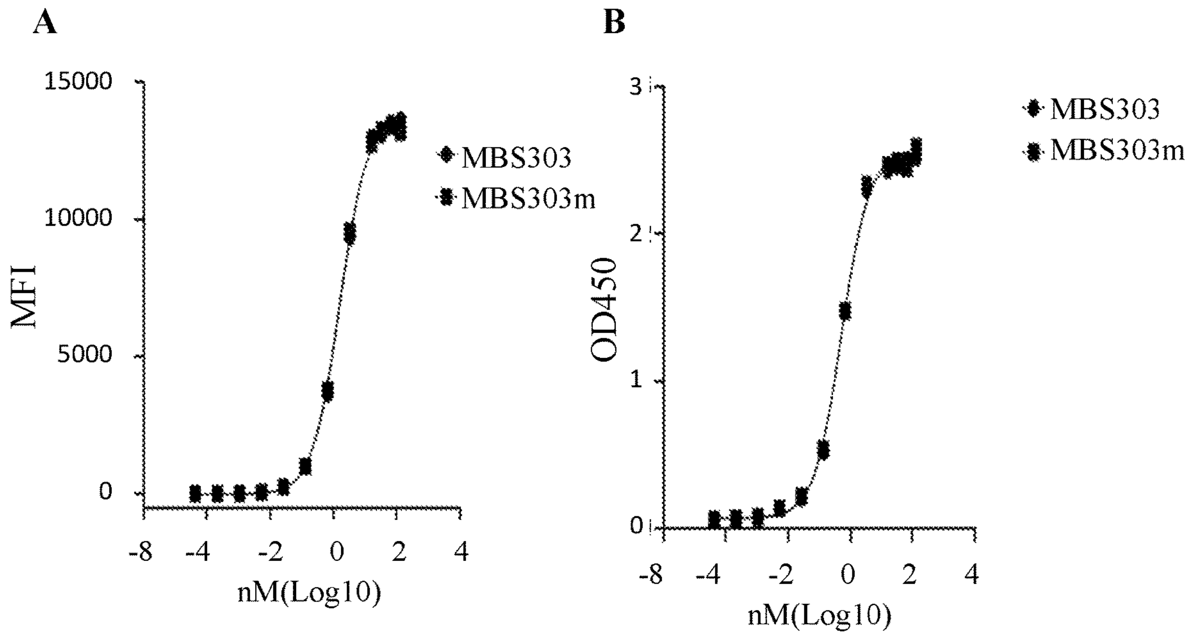
FIG. 4 shows the binding activity of two anti-TIGIT/VEGF bispecific antibodies MBS310 and MBS310m to HEK293A/human TIGIT cells (A) and human VEGF-A (B).

MBS310 and MBS310m's binding capability to TIGIT and VEGF was shown in FIG. 4, from which MBS303 and MBS303m (with 83E, 100Q and 104-106LTA) showed comparable binding activity to the TIGIT and VEGF. The data further indicated the engineering or modification at the light chain framework region(s) of the scFv had little or no influence on the bispecific antibodies' target binding capability.

Certain sequences of the application were set forth below.

| Description/Sequence and SEQ ID NO |
|---|
| VH-CDR1 of anti-CD3 antibody<br>TYAMN (SEQ ID NO: 1) |
| VH-CDR2 of anti-CD3 antibody<br>RIRSKYNNYATYYAISV (SEQ ID NO: 2) |
| VH-CDR3 of anti-CD3 antibody<br>HGNFGNSYLSYWAY (SEQ ID NO: 3) |
| VL-CDR1 of anti-CD3 antibody<br>QSSTGAVTTNNYAN (SEQ ID NO: 4) |
| VL-CDR2 of anti-CD3 antibody<br>GTKQRAP (SEQ ID NO: 5) |
| VL-CDR3 of anti-CD3 antibody<br>VLWYSNLWV (SEQ ID NO: 6) |
| VH-CDR1 of anti-CD20 antibody<br>YSWIN (SEQ ID NO: 7) |
| VH-CDR2 of anti-CD20 antibody<br>RIFPGDGDTDYNGKF (SEQ ID NO: 8) |
| VH-CDR3 of anti-CD20 antibody<br>NVFDGYWLVY (SEQ ID NO: 9) |
| VL-CDR1 of anti-CD20 antibody<br>RSSKSLLHSNGITYLY (SEQ ID NO: 10) |
| VL-CDR2 of anti-CD20 antibody<br>QMSNLVS (SEQ ID NO: 11) |

-continued

| Description/Sequence and SEQ ID NO |
|---|
| VL-CDR3 of anti-CD20 antibody<br>AQNLELPYT (SEQ ID NO: 12) |
| VH of anti-CD3 antibody<br>EVQLLESGGGLVQPGGSLRLSCAASGFTFNTYAMNWVRQAPGKGLEWVARIRSKYNNY<br>ATYYAISVKDRFTISRDDSKNTLYLQMNSLRAEDTAMYYCVRHGNFGNSYLSYWAYWG<br>QGTLVTVSS (SEQ ID NO: 13) |
| VL of anti-CD3 antibody<br>QAVVTQEPSLTVSPGGTVTLTCQSSTGAVTTNNYANWVQQKPGHAFRGLIGGTKQRAPG<br>VPA**R**FSGSLLGGKAALTLSGVQPEDEAEYYCVLWYSNLWVFGGGTKLTVL (SEQ ID NO:<br>14) |
| VH of anti-CD20 antibody<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSS (SEQ ID NO: 15) |
| VL (with wildtype framework regions) of anti-CD20 antibody<br>DIVMTQTPLSLPVTPGEPASISCRSSKSLLHSNGITYLYWYLQKPGQSPQLLIYQMSNLVSG<br>VPD**R**FSGSGSGTDFTLKISRVEAED*X1*GVYYCAQNLELPYTFGX2GTK*X3X4X5*K (SEQ ID<br>NO: 16) X1 = V, X2 = G, X3 = V, X4 = E, X5 = I<br>DIVMTQTPLSLPVTPGEPASISCRSSKSLLHSNGITYLYWYLQKPGQSPQLLIYQMSNLVSG<br>VPD**R**FSGSGSGTDFTLKISRVEAED*V*GVYYCAQNLELPYTFGGGTK*VEI*K |
| VL (with 104-106LTA) of anti-CD20 antibody<br>SEQ ID NO: 16, X1 = V, X2 = G, X3 = L, X4 = T, X5 = A<br>DIVMTQTPLSLPVTPGEPASISCRSSKSLLHSNGITYLYWYLQKPGQSPQLLIYQMSNLVSG<br>VPD**R**FSGSGSGTDFTLKISRVEAED*V*GVYYCAQNLELPYTFGGGTK*LTA*K |
| VL (with 83E) of anti-CD20 antibody<br>SEQ ID NO: 16, X1 = E, X2 = G, X3 = V, X4 = E, X5 = I<br>DIVMTQTPLSLPVTPGEPASISCRSSKSLLHSNGITYLYWYLQKPGQSPQLLIYQMSNLVSG<br>VPD**R**FSGSGSGTDFTLKISRVEAED*E*GVYYCAQNLELPYTFGGGTK*VEI*K |
| VL (with 83E, 100Q, 104-106LTA) of anti-CD20 antibody<br>SEQ ID NO: 16, X1 = E, X2 = Q, X3 = L, X4 = T, X5 = A<br>DIVMTQTPLSLPVTPGEPASISCRSSKSLLHSNGITYLYWYLQKPGQSPQLLIYQMSNLVSG<br>VPDRFSGSGSGTDFTLKISRVEAED*E*GVYYCAQNLELPYTFGQGTK*LTA*K |
| Light chain constant region of anti-CD3 antibody<br>GQP**K**AAPSVTLFPPSSEELQANKATLVCLISDFYPGAVTVAWKADSSPVKAGVETTTPSK<br>QSNNKYAASSYLSLTPEQWKSHRSYSCQVTHEGSTVEKTVAPTECS (SEQ ID NO: 17) |
| Light chain constant region of anti-CD20 antibody<br>RTVAAPSVFIFPPSDEQLKSGTASVVCLLNNFYPREAKVQWKVDNALQSGNSQESVTEQD<br>SKDSTYSLSSTLTLSKADYEKHKVYACEVTHQGLSSPVTKSFNRGEC (SEQ ID NO: 18) |
| Heavy chain constant region in MIL221-2 and MIL221-3<br>IgG1 (L234A/L235A/N297A/T366W)<br>ASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPEAAGGPS<br>VFLFPPKPKDTLMISRTPEVTCVVVDVSHEDPEVKFNWYVDGVEVHNAKTKPREEQYAS<br>TYRVVSVLTVLHQDWLNGKEYKCKVSNKALPAPIEKTIS**K**AKGQPREPQVYTLPPSREEM<br>TKNQVSLX1CX2VKGFYPSDIAVEWESNGQPENNYKTTPPVLDSDGSFFLX3SKLTVDKSR<br>WQQGNVFSCSVMHEALHNHYTQKSLSLSPGK (SEQ ID NO: 19) X1 = W, X2 = L, X3 = Y<br>ASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPEAAGGPS<br>VFLFPPKPKDTLMISRTPEVTCVVVDVSHEDPEVKFNWYVDGVEVHNAKTKPREEQYAS<br>TYRVVSVLTVLHQDWLNGKEYKCKVSNKALPAPIEKTIS**K**AKGQPREPQVYTLPPSREEM<br>TKNQVSLWCLVKGFYPSDIAVEWESNGQPENNYKTTPPVLDSDGSFFLYSKLTVDKS**R**W<br>QQGNVFSCSVMHEALHNHYTQKSLSLSPGK |
| Heavy chain constant region in MIL-220<br>SEQ ID NO: 19, X1 = S, X2 = A, X3 = V<br>IgG1 (L234A/L235A/N297A/T366S/L368A/Y407V)<br>ASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPEAAGGPS<br>VFLFPPKPKDTLMISRTPEVTCVVVDVSHEDPEVKFNWYVDGVEVHNAKTKPREEQYAS<br>TYRVVSVLTVLHQDWLNGKEYKCKVSNKALPAPIEKTIS**K**AKGQPREPQVYTLPPSREEM<br>TKNQVSLSCAVKGFYPSDIAVEWESNGQPENNYKTTPPVLDSDGSFFLVSKLTVDKSRWQ<br>QGNVFSCSVMHEALHNHYTQKSLSLSPGK |

-continued

| Description/Sequence and SEQ ID NO |
|---|
| MIL221-2's long chain (heavy chain constant region with a knob, scFv with wildtype VL framework regions) in MBS303<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSSGGGGSGGGGSGGGGSDIVMTQTPLSLPVTPGEPASISCRSSKSLLHSNGITYLYWYLQ<br>KPGQSPQLLIYQMSNLVSGVPDRFSGSGSGTDFTLKISRVEAEDVGVYYCAQNLELPYTFG<br>GGTKVEIKGGGGSGGGGSGGGGSEVQLLESGGGLVQPGGSLRLSCAASGFTFNTYAMNW<br>VRQAPGKGLEWVARIRSKYNNYATYYAISVKDRFTISRDDSKNTLYLQMNSLRAEDTAM<br>YYCVRHGNFGNSYLSYWAYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQTYICNVNHKPS<br>NTKVDKKVEPKSCDKTHTCPPCPAPEAAGGPSVFLFPPKPKDTLMISRTPEVTCVVVDVS<br>HEDPEVKFNWYVDGVEVHNAKTKPREEQYASTYRVVSVLTVLHQDWLNGKEYKCKVS<br>NKALPAPIEKTISKAKGQPREPQVYTLPPSREEMTKNQVSLWCLVKGFYPSDIAVEWESN<br>GQPENNYKTTPPVLDSDGSFFLYSKLTVDKSRWQQGNVFSCSVMHEALHNHYTQKSLSL<br>SPGK (SEQ ID NO: 30) |
| MIL221-3's long chain (heavy chain constant region with a knob, scFv with VL containing 83E/100Q/104-106LTA) in MBS303m<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSSGGGGSGGGGSGGGGSGGGGSDIVMTQTPLSLPVTPGEPASISCRSSKSLLHSNGITYL<br>YWYLQKPGQSPQLLIYQMSNLVSGVPDRFSGSGSGTDFTLKISRVEAEDX1GVYYCAQNL<br>ELPYTFGX2GTKX3X4X5KGGGGSGGGGSGGGGSEVQLLESGGGLVQPGGSLRLSCAASG<br>FTFNTYAMNWVRQAPGKGLEWVARIRSKYNNYATYYAISVKDRFTISRDDSKNTLYLQ<br>MNSLRAEDTAMYYCVRHGNFGNSYLSYWAYWGQGTLVTVSSASTKGPSVFPLAPSSKS<br>TSGGTAALGCLVKDYFPEPVTVSWNSGALTSGVHTFPAVLQSSGLYSLSSVVTVPSSSLGT<br>QTYICNVNHKPSNTKVDKKVEPKSCDKTHTCPPCPAPEAAGGPSVFLFPPKPKDTLMISRT<br>PEVTCVVVDVSHEDPEVKFNWYVDGVEVHNAKTKPREEQYASTYRVVSVLTVLHQDWL<br>NGKEYKCKVSNKALPAPIEKTISKAKGQPREPQVYTLPPSREEMTKNQVSLWCLVKGFYP<br>SDIAVEWESNGQPENNYKTTPPVLDSDGSFFLYSKLTVDKSRWQQGNVFSCSVMHEALH<br>NHYTQKSLSLSPGK (SEQ ID NO: 20), X1 = E, X2 = Q, X3 = L, X4 = T, X5 = A<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSSGGGGSGGGGSGGGGSGGGGSDIVMTQTPLSLPVTPGEPASISCRSSKSLLHSNGITYL<br>YWYLQKPGQSPQLLIYQMSNLVSGVPDRFSGSGSGTDFTLKISRVEAEDEGVYYCAQNLE<br>LPYTFGQGTKLTAKGGGGSGGGGSGGGGSEVQLLESGGGLVQPGGSLRLSCAASGFTFNT<br>YAMNWVRQAPGKGLEWVARIRSKYNNYATYYAISVKDRFTISRDDSKNTLYLQMNSLR<br>AEDTAMYYCVRHGNFGNSYLSYWAYWGQGTLVTVSSASTKGPSVFPLAPSSKSTSGGTA<br>ALGCLVKDYFPEPVTVSWNSGALTSGVHTFPAVLQSSGLYSLSSVVTVPSSSLGTQTYICN<br>VNHKPSNTKVDKKVEPKSCDKTHTCPPCPAPEAAGGPSVFLFPPKPKDTLMISRTPEVTCV<br>VVDVSHEDPEVKFNWYVDGVEVHNAKTKPREEQYASTYRVVSVLTVLHQDWLNGKEY<br>KCKVSNKALPAPIEKTISKAKGQPREPQVYTLPPSREEMTKNQVSLWCLVKGFYPSDIAVE<br>WESNGQPENNYKTTPPVLDSDGSFFLYSKLTVDKSRWQQGNVFSCSVMHEALHNHYTQ<br>KSLSLSPGK |
| MIL221-3's long chain (heavy chain constant region with a knob, scFv with VL containing 104-106LTA) in MBS303m<br>SEQ ID NO: 20, X1 = V, X2 = G, X3 = L, X4 = T, X5 = A<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSSGGGGSGGGGSGGGGSGGGGSDIVMTQTPLSLPVTPGEPASISCRSSKSLLHSNGITYL<br>YWYLQKPGQSPQLLIYQMSNLVSGVPDRFSGSGSGTDFTLKISRVEAEDVGVYYCAQNLE<br>LPYTFGGGTKLTAKGGGGSGGGGSGGGGSEVQLLESGGGLVQPGGSLRLSCAASGFTFNT<br>YAMNWVRQAPGKGLEWVARIRSKYNNYATYYAISVKDRFTISRDDSKNTLYLQMNSLR<br>AEDTAMYYCVRHGNFGNSYLSYWAYWGQGTLVTVSSASTKGPSVFPLAPSSKSTSGGTA<br>ALGCLVKDYFPEPVTVSWNSGALTSGVHTFPAVLQSSGLYSLSSVVTVPSSSLGTQTYICN<br>VNHKPSNTKVDKKVEPKSCDKTHTCPPCPAPEAAGGPSVFLFPPKPKDTLMISRTPEVTCV<br>VVDVSHEDPEVKFNWYVDGVEVHNAKTKPREEQYASTYRVVSVLTVLHQDWLNGKEY<br>KCKVSNKALPAPIEKTISKAKGQPREPQVYTLPPSREEMTKNQVSLWCLVKGFYPSDIAVE<br>WESNGQPENNYKTTPPVLDSDGSFFLYSKLTVDKSRWQQGNVFSCSVMHEALHNHYTQ<br>KSLSLSPGK |
| MIL221-3's long chain (heavy chain constant region with a knob, scFv with VL containing 83E) in MBS303m<br>SEQ ID NO: 20, X1 = E, X2 = G, X3 = V, X4 = E, X5 = I<br>QVQLVQSGAEVKKPGSSVKVSCKASGYAFSYSWINWVRQAPGQGLEWMGRIFPGDGDT<br>DYNGKFKGRVTITADKSTSTAYMELSSLRSEDTAVYYCARNVFDGYWLVYWGQGTLVT<br>VSSGGGGSGGGGSGGGGSGGGGSDIVMTQTPLSLPVTPGEPASISCRSSKSLLHSNGITYL<br>YWYLQKPGQSPQLLIYQMSNLVSGVPDRFSGSGSGTDFTLKISRVEAEDEGVYYCAQNLE<br>LPYTFGGGTKVEIKGGGGSGGGGSGGGGSEVQLLESGGGLVQPGGSLRLSCAASGFTFNT<br>YAMNWVRQAPGKGLEWVARIRSKYNNYATYYAISVKDRFTISRDDSKNTLYLQMNSLR<br>AEDTAMYYCVRHGNFGNSYLSYWAYWGQGTLVTVSSASTKGPSVFPLAPSSKSTSGGTA<br>ALGCLVKDYFPEPVTVSWNSGALTSGVHTFPAVLQSSGLYSLSSVVTVPSSSLGTQTYICN<br>VNHKPSNTKVDKKVEPKSCDKTHTCPPCPAPEAAGGPSVFLFPPKPKDTLMISRTPEVTCV |

-continued

Description/Sequence and SEQ ID NO

VVDVSHEDPEVKFNWYVDGVEVHNAKTKPREEQYASTYRVVSVLTVLHQDWLNGKEY
KCKVSNKALPAPIEKTISKAKGQPREPQVYTLPPSREEMTKNQVSLWCLVKGFYPSDIAVE
WESNGQPENNYKTTPPVLDSDGSFFLYSKLTVDKSRWQQGNVFSCSVMHEALHNHYTQ
KSLSLSPGK

MIL220's long chain (heavy chain constant region with a hole) in MBS303
QVQLVQSGAEVKKPGSSVKVSCKASGYAFSYSWINWVRQAPGQGLEWMGRIFPGDGDT
DYNGKFKGRVTITADKSTSTAYMELSSLRSEDTAVYYCARNVFDGYWLVYWGQGTLVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPEAAG
GPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSR
EEMTKNQVSLSCAVKGFYPSDIAVEWESNGQPENNYKTTPPVLDSDGSFFLVSKLTVDKS
RWQQGNVFSCSVMHEALHNHYTQKSLSLSPGK (SEQ ID NO: 21)

MIL221-2 and ML221-3's short chain
QAVVTQEPSLTVSPGGTVTLTCQSSTGAVTTNNYANWVQQKPGHAFRGLIGGTKQRAPG
VPARFSGSLLGGKAALTLSGVQPEDEAEYYCVLWYSNLWVFGGGTKLTVLGQPKAAPSV
TLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS (SEQ ID NO: 22)

MIL220's short chain
DIVMTQTPLSLPVTPGEPASISCRSSKSLLHSNGITYLYWYLQKPGQSPQLLIYQMSNLVSG
VPDRFSGSGSGTDFTLKISRVEAEDVGVYYCAQNLELPYTFGGGTKVEIKRTVAAPSVFIF
PPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 23)

VL (with wildtype framework regions) of anti-TIGIT antibody
EIVLTQSPGTLSLSPGERATMTCRASSSISSTYLHWYQQKPGASPKLLIYNTQNLASGVPA
RFSGSGSGTSYTLTISRLEPEDX1AVYYCQQFGGYPLITFGAGTKLX2X3KR (SEQ ID NO:
24) X1 = F, X2 = E, X3 = L
EIVLTQSPGTLSLSPGERATMTCRASSSISSTYLHWYQQKPGASPKLLIYNTQNLASGVPA
RFSGSGSGTSYTLTISRLEPEDFAVYYCQQFGGYPLITFGAGTKLELKR VL (with 83E/104-106LTA) of anti-TIGIT antibody
SEQ ID NO: 24, X1 = E, X2 = T, X3 = A
EIVLTQSPGTLSLSPGERATMTCRASSSISSTYLHWYQQKPGASPKLLIYNTQNLASGVPA
RFSGSGSGTSYTLTISRLEPED*E*AVYYCQQFGGYPLITFGAGTK*LTA*KR MBS310's long chain (scFv with wildtype framework regions)
EVQLVESGGGLVQPGGSLRLSCAASGYTFTNYGMNWVRQAPGKGLEWVGWINTYTGEP
TYAADFKRRFTFSLDTSKSTAYLQMNSLRAEDTAVYYCAKYPHYYGSSHWYFDVWGQG
TLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGAGGGGSGGGGSGGGGSQVQLVQSG
AEVKKPGASVKVSCKASGYTFTSYNVHWVRQAPGQGLEWMGTIYPGNLATSYNQKFKG
RVTLTADTSTSTVYMELSSLRSEDTAVYYCARSGTMDYWGQGTTVTVSSGGGGSGGGG
SGGGGSGGGGSEIVLTQSPGTLSLSPGERATMTCRASSSISSTYLHWYQQKPGASPKLLIY
NTQNLASGVPARFSGSGSGTSYTLTISRLEPEDX1AVYYCQQFGGYPLITFGAGTKLX2X3
KR (SEQ ID NO: 25) X1 = F, X2 = E, X3 = L
EVQLVESGGGLVQPGGSLRLSCAASGYTFTNYGMNWVRQAPGKGLEWVGWINTYTGEP
TYAADFKRRFTFSLDTSKSTAYLQMNSLRAEDTAVYYCAKYPHYYGSSHWYFDVWGQG
TLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGAGGGGSGGGGSGGGGSQVQLVQSG
AEVKKPGASVKVSCKASGYTFTSYNVHWVRQAPGQGLEWMGTIYPGNLATSYNQKFKG
RVTLTADTSTSTVYMELSSLRSEDTAVYYCARSGTMDYWGQGTTVTVSSGGGGSGGGG
SGGGGSGGGGSEIVLTQSPGTLSLSPGERATMTCRASSSISSTYLHWYQQKPGASPKLLIY
NTQNLASGVPARFSGSGSGTSYTLTISRLEPEDFAVYYCQQFGGYPLITFGAGTKLELKR MBS310m's long chain (scFv with VL having 83E/104-106LTA)
SEQ ID NO: 25, X1 = E, X2 = T, X3 = A
EVQLVESGGGLVQPGGSLRLSCAASGYTFTNYGMNWVRQAPGKGLEWVGWINTYTGEP
TYAADFKRRFTFSLDTSKSTAYLQMNSLRAEDTAVYYCAKYPHYYGSSHWYFDVWGQG
TLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGAGGGGSGGGGSGGGGSQVQLVQSG
AEVKKPGASVKVSCKASGYTFTSYNVHWVRQAPGQGLEWMGTIYPGNLATSYNQKFKG -continued

| Description/Sequence and SEQ ID NO |
|---|
| RVTLTADTSTSTVYMELSSLRSEDTAVYYCARSGTMDYWGQGTTVTVSSGGGGSGGGG<br>SGGGGSGGGGSEIVLTQSPGTLSLSPGERATMTCRASSSISSTYLHWYQQKPGASPKLLIY<br>NTQNLASGVPARFSGSGSGTSYTLTISRLEPED*E*AVYYCQQFGGYPLITFGAGTK*LTA*KR |
| MBS310 and MBS310m's short chain<br>DIQMTQSPSSLSASVGDRVTITCSASQDISNYLNWYQQKPGKAPKVLIYFTSSLHSGVPSRF<br>SGSGSGTDFTLTISSLOPEDFATYYCQQYSTVPWTFGQGTKVEIKRTVAAPSVFIFPPSDEQ<br>LKSGTASVVCLLNNFYPREAKVQWKVDNALQSGNSQESVTEQDSKDSTYSLSSTLTLSK<br>ADYEKHKVYACEVTHQGLSSPVTKSFNRGEC (SEQ ID NO: 26) |
| Linker<br>GGGGSGGGGSGGGGS (SEQ ID NO: 27)<br>GGGGSGGGGSGGGGSGGGGS (SEQ ID NO: 28)<br>GGGGSGGGGSGGGGSGGGGSGGGGS (SEQ ID NO: 29) |
| Human TIGIT<br>MRWCLLLIWAQGLRQAPLASGMMTGTIETTGNISAEKGGSIILQCHLSSTTAQVTQVNWE<br>QQDQLLAICNADLGWHISPSFKDRVAPGPGLGLTLQSLTVNDTGEYFCIYHTYPDGTYTG<br>RIFLEVLESSVAEHGARFQIPLLGAMAATLVVICTAVIVVVALTRKKKALRIHSVEGDLRR<br>KSAGQEEWSPSAPSPPGSCVQAEAAPAGLCGEQRGEDCAELHDYFNVLSYRSLGNCSFFT<br>ETG (SEQ ID NO: 31) |
| First framework region of VL<br>DIVMTQTPLSLPVTPGEPASISC (SEQ ID NO: 36) |
| Second framework region of VL<br>WYLQKPGQSPQLLIY (SEQ ID NO: 37) |
| Third framework region of VL (with or without 83E)<br>GVPDRFSGSGSGTDFTLKISRVEAEDXGVYYC (SEQ ID NO: 32)<br>X = V or E |
| Fourth framework region of VL (with 104-106LTA or 100Q/104-106LTA)<br>FGXGTKLTAK (SEQ ID NO: 33)<br>X = G or Q |
| First framework region of VL<br>EIVLTQSPGTLSLSPGERATMTC (SEQ ID NO: 38) |
| Second framework region of VL<br>WYQQKPGASPKLLIY (SEQ ID NO: 39) |
| Third framework region of VL (with or without 83E)<br>GVPARFSGSGSGTSYTLTISRLEPEDXAVYYC (SEQ ID NO: 34)<br>X = F or E |
| Fourth framework region of VL (with 104-106LTA)<br>FGAGTK*LTA*KR (SEQ ID NO: 35) |

While the application has been described above in connection with one or more embodiments, it should be understood that the application is not limited to those embodiments, and the description is intended to cover all alternatives, modifications, and equivalents, as may be included within the spirit and scope of the appended claims. All referenced cited herein are further incorporated by reference in their entirety.

The invention claimed is:

1. A single chain fragment variable (scFv), comprising a heavy chain variable region, a linker and a κ light chain variable region, wherein the κ light chain variable region comprises a first framework region, a second framework region, a third framework region, and a fourth framework region, wherein the κ light chain variable region is engineered to comprise leucine (L), threonine (T) and alanine (A) at Position 104 to 106 according to Kabat numbering scheme, wherein the heavy chain variable region comprises the amino acid sequence of SEQ ID NO: 15, and the light chain variable region comprises the amino acid sequence DIVMTQTPLSLPVTPGEPASISCRSSKSLLHSNGITYLYWYLQKPGQSPQLLIYQMSNLVSGVPDRFSGSGSGTDFTLKISRVEAEDXiGVYYCAQNLELPYTFG$X_2$GTK$X_3X_4X_5$K (SEQ ID NO: 16), wherein $X_1$, $X_2$, $X_3$, $X_4$ and $X_5$ are V, G, L, T and A, respectively; or E, Q, L, T and A, respectively.

2. A bispecific antibody specifically binding CD3 and CD20, comprising an anti-CD3 Fab, an anti-CD20 Fab, and an anti-CD20 single chain fragment variable (scFv), wherein the anti-CD20 scFv is the scFv according to claim 1.

3. The bispecific antibody according to claim 2, comprising a first polypeptide chain, a second polypeptide chain, a third polypeptide chain, and a fourth polypeptide chain, wherein the first, the second, the third and the fourth polypeptide chains comprise the amino acid sequences QVQLVQSGAEVKKPGSSVKVSCKASGYAFSYSWINWVRQAPGQGLEWMGRIFPGDGDTDYNGKFKGRVTITADKSTSTAYMELSSLRSEDTAVYYCARNVFDGYWLVYWGQGTLVTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTK PREEQYASTYRVVSVLTVLHQDWLNGKEYKCKVSNKALPAPIEKTISKAKGQPREPQV YTLPPSREEMTKNQVSLSCAVKGFYPSDIAVEWESNGQPENNYKTTPPVLDSDGSFFLVS KLTVDKSRWQQGNVFSCSVMHEALHNHYTQKSLSLSPGK (SEQ ID NO: 21), DIVMTQTPLSLPVTPGEPASISCRSSKSLLHSNGITYLYWYLQKPGQSPQLLIYQMSNLVS GVPDRFSGSGSGTDFTLKISRVEAEDVGVYYCAQNLELPYTFGGGTKVEIKRTVAAPSV FIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 23), QVQLVQSGAEVKKPGSSVKVSCKASGYAFSYSWINWVRQAPGQGLEWMGRIFPGDGD TDYNGKFKGRVTITADKSTSTAYMELSSLRSEDTAVYYCARNVFDGYWLVYWGQGTL VTVSSGGGGSGGGGSGG- GGSGGGGSDIVMTQTPLSLPVTPGEPASISCRSSKSLLHSNGI TYLYWYLQKPGQSPQLLIYQMSNLVSGVPDRFSGSGSGTDFTLKISRVEAEDXiGVYYC AQNLELPYTFG$X_2$ GTK$X_3X_4X_5$KGGGGSGGGGSGGGGSEVQLLESGGGLVQPGGSLRLSC AASGFTFNTYAMNWVRQAPGKGLEWVARIRSKYNNYATYYAISVKDRFTISRDDSKNT LYLQMNSLRAEDTAMYYCVRHGNFGNSYLSYWAYWGQGTLVTVSSASTKGPSVFPLA PSSKSTSGGTAALGCLVKDYFPEPVTVSWNSGALTSGVHTFPAVLQSSGLYSLSSVVTVP SSSLGTQTYICNVNHKPSNTKVDKKVEPKSCDKTHTCPPCPAPEAAGGPSVFLFPPKPKD TLMISRTPEVTCVVVDVSHEDPEVKFNWYVDGVEVHNAKTKPREEQYASTYRVVSVLT VLHQDWLNGKEYKCKVSNKALPAPIEKTISKAKGQPREPQVYTLPPSREEMTKNQVSL WCLVKGFYPSDIAVEWESNGQPENNYKTTPPVLDSDGSFFLYSKLTVDKSRWQQGNVF SCSVMHEALHNHYTQKSLSLSPGK (SEQ ID NO: 20) and QAVVTQEPSLTVSPGGTVTLTCQSSTGAVTTNNYANW- VQQKPGHAFRGLIGGTKQRAP GVPARFSGSLLGGKAALTLSGVQPEDEAEYYCVLWYSNLWVFGGGTKLTVLGQPKAAP SVTLFPPSSEELQANKATLVCLISDFYPGAVTVAWKADSSPVKAGVETTTPSKQSNNKY AASSYLSLTPEQWKSHRSYSCQVTHEGSTVEKTVAPTECS (SEQ ID NO: 22), respectively, wherein $X_1$, $X_2$, $X_3$, $X_4$ and $X_5$ in SEQ ID NO: 20 are E, Q, L, T and A, respectively; or V, G, L, T and A, respectively.

4. A nucleic acid molecule encoding the scFv according to claim 1.

5. An expression vector comprising the nucleic acid molecule according to claim 4.

6. A host cell comprising the expression vector according to claim 5.

7. The bispecific antibody according to claim 2, wherein the anti-CD3 Fab comprises a heavy chain variable region CDR1 ($V_H$-CDR1), a $V_H$-CDR2, a $V_H$-CDR3, a light chain variable region ($V_L$-CDR1), a $V_L$-CDR2 and a $V_L$-CDR3 comprising the amino acid sequences TYAMN (SEQ ID NO: 1), RIRSKYNNYATYYAISV (SEQ ID NO: 2), HGNFGNSYLSYWAY (SEQ ID NO: 3), QSSTGAVTTNNYAN (SEQ ID NO: 4), GTKQRAP (SEQ ID NO: 5) and VLWYSNLWV (SEQ ID NO: 6), respectively, and the anti-CD20 Fab comprises a $V_H$-CDR1, a $V_H$-CDR2, a $V_H$-CDR3, a $V_L$-CDR1, a $V_L$-CDR2 and a $V_L$-CDR3 comprising the amino acid sequences YSWIN (SEQ ID NO: 7), RIFPGDGDTDYNGKF (SEQ ID NO: 8), NVFDGYWLVY (SEQ ID NO: 9), RSSKSLLHSNGITYLY (SEQ ID NO: 10), QMSNLVS (SEQ ID NO: 11) and AQNLELPYT (SEQ ID NO: 12), respectively.

8. The bispecific antibody according to claim 7, wherein the anti-CD3 Fab comprises a heavy chain variable region and a light chain variable region comprising the amino acid sequences EVQLLESGGGLVQPGGSLRLSCAASGFTFNTYAMNWVRQAPGKGLEWVARIRSKYNNYATYYAIS- VKDRFTISRDDSKNTLYLQMNSLRAEDTAMYYCV-RHGNFGNSYLSYWAY WGQGTLVTVSS (SEQ ID NO: 13) and QAVVTQEPSLTVSPGGTVTLTCQSSTGAVTTN-NYANWVQQKPGHAFRGLIGGTKQRAP GVPARFSG-SLLGGKAALTLSGVQPEDEAEYYCVLWYSNLW-VFGGGTKLTVL (SEQ ID NO: 14), respectively, and the anti-CD20 Fab comprises a heavy chain variable region and a light chain variable region comprising the amino acid sequences QVQLVQSGAEVKKPGSSVKVSCKASGYAF-SYSWINWVRQAPGQGLEWMGRIFPGDGD TDYNGK-FKGRVTITADKSTSTAYMEL SSLRSEDTAVYYCAR-NVFDGYWLVYWGQGTL VTVSS (SEQ ID NO: 15) and DIVMTQTPLSLPVTPGEPASISCRSSKSLLHSNGITY-LYWYLQKPGQSPQLLIYQMSNLVSGVPDRFSGSGS-GTDFTLKISRVEAEDXiGVYYCAQNLELPYTFG$X_2$ GTK$X_3X_4X_5$K (SEQ ID NO: 16), respectively, wherein $X_1$, $X_2$, $X_3$, $X_4$ and $X_5$ in SEQ ID NO: 16 are V, G, V, E and I, respectively.

9. The bispecific antibody according to claim 8, comprising:

i) a first polypeptide chain, comprising the anti-CD20 heavy chain variable region, and a heavy chain constant region, wherein the heavy chain constant region comprises a CH1, a CH2 and a CH3;

ii) a second polypeptide chain, comprising the anti-CD20 light chain variable region and a light chain constant region;

iii) a third polypeptide chain, comprising the anti-CD20 scFv, the anti-CD3 heavy chain variable region, and a heavy chain constant region, wherein the heavy chain constant region comprises a CH1, a CH2 and a CH3, and iv) a fourth polypeptide chain, comprising the anti-CD3 light chain variable region and a light chain constant region, wherein the anti-CD20 heavy chain variable region and the heavy chain constant region CH1 in the first polypeptide chain associate with the anti-CD20 light chain variable region and the light chain constant region in the second polypeptide chain to form the anti-CD20 Fab, the anti-CD3 heavy chain variable region and the heavy chain constant region CH1 in the third polypeptide chain associate with the anti-CD3 light chain variable region and the light chain constant region in the fourth polypeptide chain to form the anti-CD3 Fab.

10. The bispecific antibody according to claim 9, wherein the heavy chain constant region in the first polypeptide chain is an IgG1 heavy chain constant region with L234A/L235A/N297A/T366W mutations, and the heavy chain constant region in the third polypeptide chain is an IgG1 heavy chain constant region with L234A/L235A/N297A/T366S/L368A/Y407V mutations, or the heavy chain constant region in the first polypeptide chain is an IgG1 heavy chain constant region with L234A/L235A/N297A/T366S/L368A/Y407V mutations, and the heavy chain constant region in the third polypeptide chain is an IgG1 heavy chain constant region with L234A/L235A/N297A/T366W mutations.

11. The bispecific antibody according to claim 10, wherein the first polypeptide chain comprises, from N-terminus to C-terminus, the anti-CD20 heavy chain variable region, the CH1, the CH2 and the CH3, the second polypeptide chain comprises, from N-terminus to C-terminus, the anti-CD20 light chain variable region and the light chain constant region, the third polypeptide chain comprises, from N-terminus to C-terminus, the anti-CD20 scFv, the anti-CD3 heavy chain variable region, the CH1, the CH2 and the CH3, the fourth polypeptide chain comprises, from N-terminus to C-terminus, the anti-CD3 light chain variable region and the light chain constant region.

12. A pharmaceutical composition comprising the bispecific antibody according to claim 2.

13. A method for treating or alleviating a B cell associated disease in a subject in need thereof, comprising administering to the subject a therapeutically effective amount of the pharmaceutical composition according to claim 12, wherein the B cell associated disease is B-cell lymphoma, B-cell leukemia, or a B cell-mediated autoimmune disease.

* * * * *